United States Patent [19]

Abe et al.

[11] Patent Number: 5,107,041

[45] Date of Patent: Apr. 21, 1992

[54] 1,1-DICYCLOHEXYL CYCLOALKANE DERIVATIVE, METHOD FOR THE PREPARATION THEREOF AND TRACTION-DRIVE FLUID CONTAINING THE SAME

[75] Inventors: Kazuaki Abe; Toshiyuki Tsubouchi, both of Sodegaura; Hitoshi Hata, Ichihara, all of Japan

[73] Assignee: Idemitsu Kosan Co., Ltd., Tokyo, Japan

[21] Appl. No.: 406,688

[22] Filed: Sep. 13, 1989

[30] Foreign Application Priority Data

Sep. 30, 1988 [JP] Japan .................. 63-246880
Apr. 25, 1989 [JP] Japan .................. 1-103381

[51] Int. Cl.$^5$ .................. C07C 13/18; C07C 13/24; C07C 13/25; C07C 13/271
[52] U.S. Cl. .................. 585/20; 252/9; 252/73; 585/21
[58] Field of Search .................. 252/9, 73; 585/20, 21, 585/22

[56] References Cited

U.S. PATENT DOCUMENTS 4,556,503 12/1985 Tsubouchi et al. .................. 585/20
4,604,492 8/1986 Shimizu et al. .................. 585/360
4,704,843 11/1988 Segnitz et al. .................. 585/20

FOREIGN PATENT DOCUMENTS 0135871 4/1985 European Pat. Off. .
362673 4/1990 European Pat. Off. .................. 585/20

Primary Examiner—Asok Pal

Attorney, Agent, or Firm—Frishauf, Holtz, Goodman & Woodward

[57] ABSTRACT

The invention provides a novel compound 1,1-dicyclohexyl cycloalkane derivative represented by the general formula

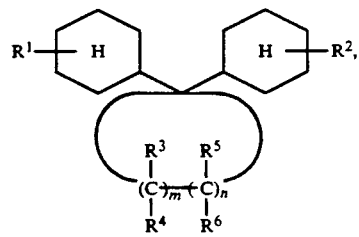

in which $R^1$ and $R^2$ are each a hydrogen atom or lower alkyl group, $R^3$ to $R^6$ are each a hydrogen atom, lower alkyl group or alkylene group forming a ring structure together with either one of the others and the carbon atom in the cycloalkane ring, and m and n are each zero or a positive integer not exceeding 6 with the proviso that m+n is 4-6, such as 1,1-dicyclohexyl cyclohexane. The compound has a relatively low viscosity and high traction coefficient even at elevated temperatures so that it is useful as a constituent of a traction-drive fluid usable in a compact and light-weight traction-drive apparatus. The compound can be synthesized by subjecting a corresponding 1,1-di(hydroxyphenyl) cycloalkane compound to a hydrogenation reaction and dehydration reaction in combination in the simultaneous presence of a hydrogenation catalyst and a dehydration catalyst.

6 Claims, 32 Drawing Sheets

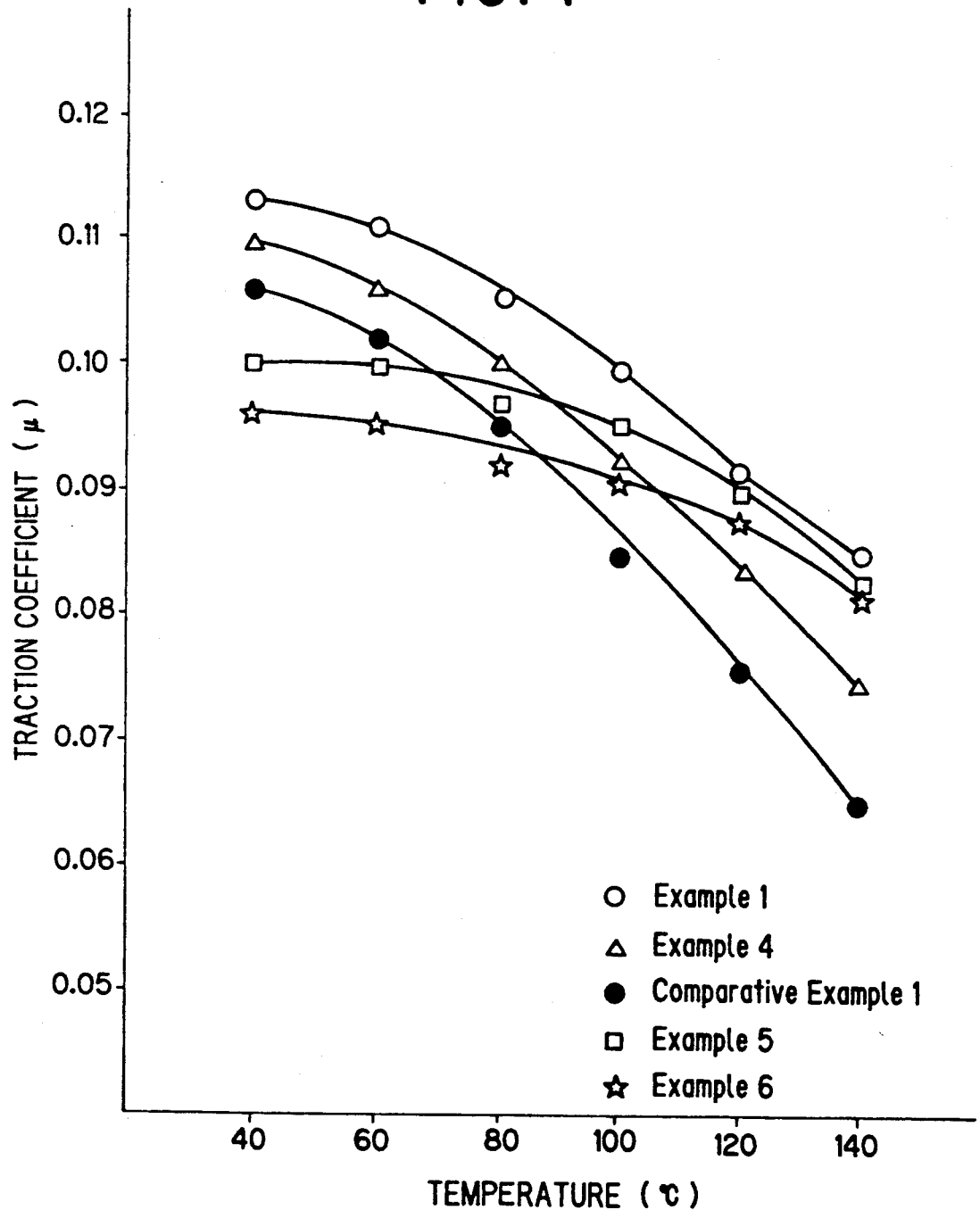

MASS NUMBER

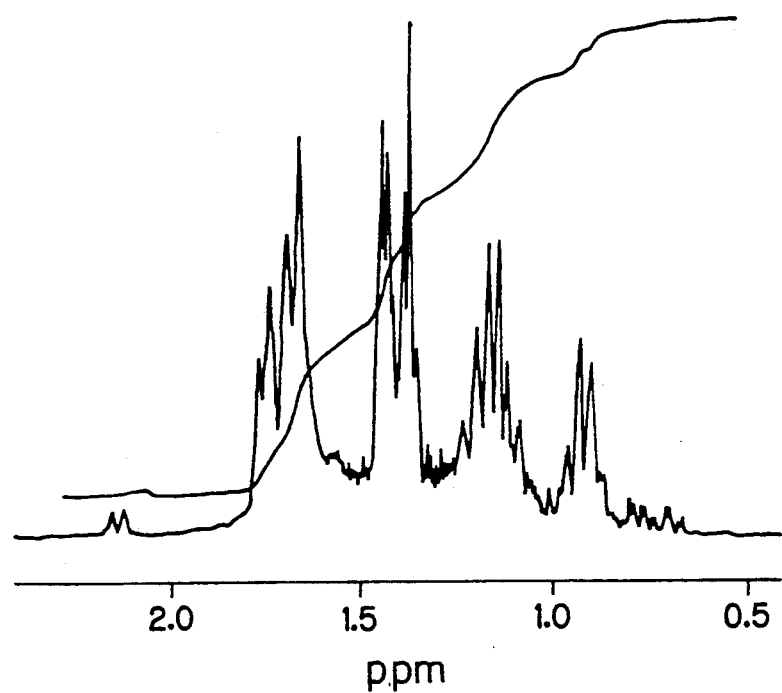
FIG. IIB

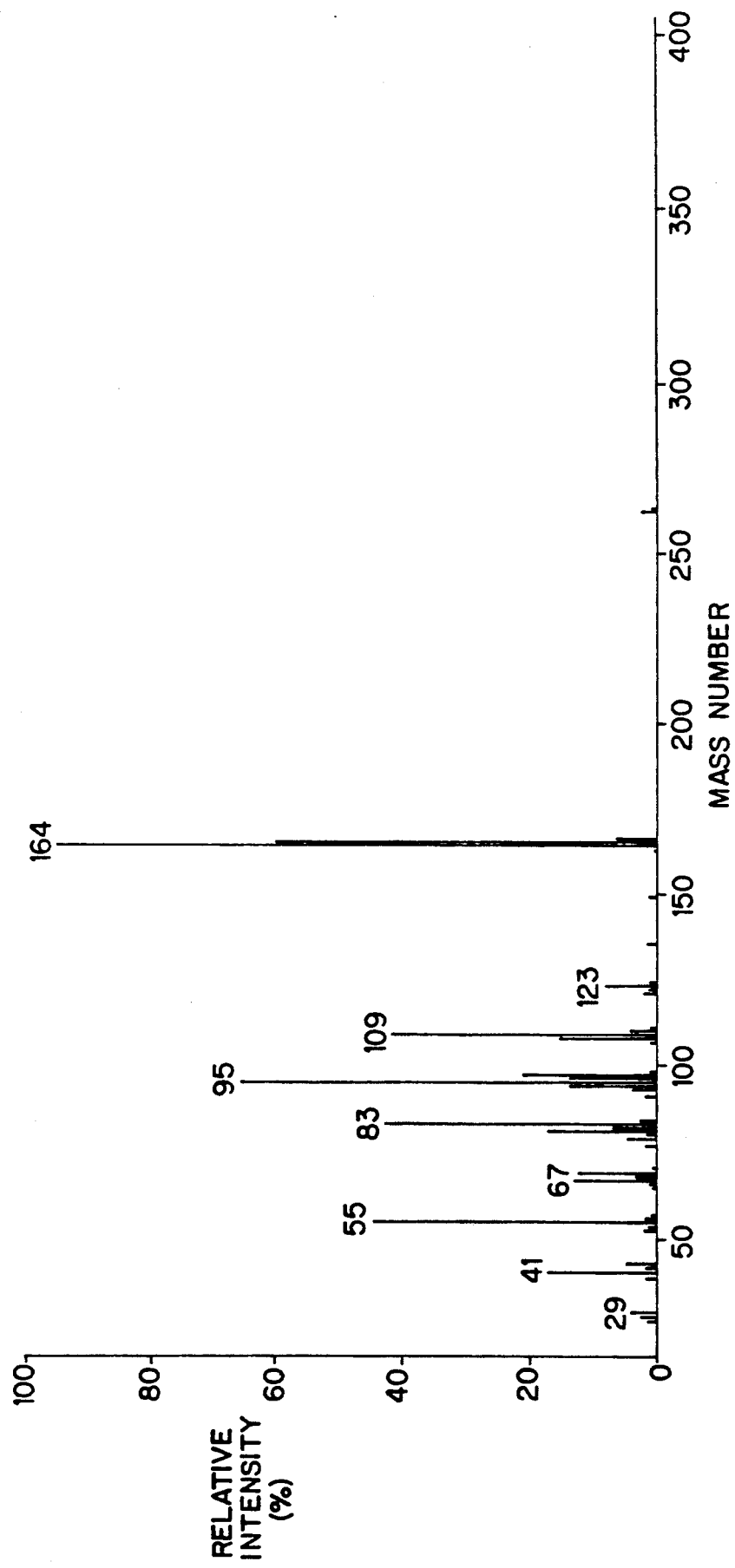

MASS NUMBER

MASS NUMBER

MASS NUMBER

1,1-DICYCLOHEXYL CYCLOALKANE DERIVATIVE, METHOD FOR THE PREPARATION THEREOF AND TRACTION-DRIVE FLUID CONTAINING THE SAME

BACKGROUND OF THE INVENTION

The present invention relates to a derivative of a 1,1-dicyclohexyl cycloalkane, which is a novel compound not known in the prior art, a method for the preparation of the compound and a traction-drive fluid containing the compound.

One of the important technological issues in the automobile industry is to develop a compact and light-weight traction-drive apparatus. Needless to say, a compact and light-weight traction-drive apparatus cannot be developed without a high-performance traction-drive fluid used therein. Accordingly, the requirements for the performance of traction-drive fluids are increasing in recent years to withstand the use under extremely severe conditions or, in particular, to exhibit high performance with stability in a wide temperature range from low temperatures to high temperatures. For example, traction-drive fluids are required to have a high traction coefficient in a temperature range from low to high temperatures, low viscosity, excellent oxidation resistance and the like among various kinds of other properties.

In the prior art, proposals have been made in Japanese Patent Publications 46-338 and 46-339 for the use of a variety of compounds as a constituent of a traction-drive fluid. None of the prior art traction-drive fluids, however, can fully satisfy the above mentioned requirements for the properties of a high-performance fluid. For example, compounds having a high traction coefficient at high temperature generally have a defect that the viscosity of the compound is unduly high at room temperature and is rapidly increased as the temperature is decreased resulting in poor flowability and a great energy loss by agitation and thus the efficiency of power transmission is lowered. On the other hand, a compound having a low viscosity at room temperature to exhibit a high efficiency of power transmission at low temperatures usually has an unduly low traction coefficient at high temperatures and the viscosity thereof at high temperatures is so low that drawbacks are sometimes caused in the lubrication of the traction-transmission apparatus filled therewith.

SUMMARY OF THE INVENTION

The present invention accordingly has an object to provide a novel compound which can be a constituent of a traction-drive fluid capable of satisfying all of the above mentioned requirements for a high-performance fluid by possessing a low viscosity at low temperature and a high traction coefficient at high temperatures, these properties of the fluid being maintained even when the compound is blended with other compounds. Another object of the invention is to provide a method for the preparation of such a compound Thus, the novel compound provided by the invention is a 1,1-dicyclohexyl cycloalkane derivative represented by the general formula

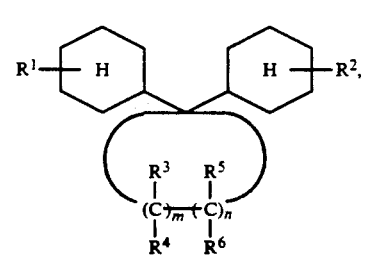

in which $R^1$ and $R^2$ are each, independently from the other, a hydrogen atom or a lower alkyl group, $R^3$, $R^4$, $R^5$ and $R^6$ are each, independently from the others, a hydrogen atom, a lower alkyl group or an alkylene group forming a ring structure together with either one of the others and the carbon atom in the cycloalkane ring to which the group is bonded, and the subscripts m and n are each zero or a positive integer not exceeding 6 with the proviso that m+n is 4, 5 or 6.

The above defined 1,1-dicyclohexyl cycloalkane derivative can be prepared by subjecting a 1,1-di(hydroxyphenyl) cycloalkane compound represented by the general formula

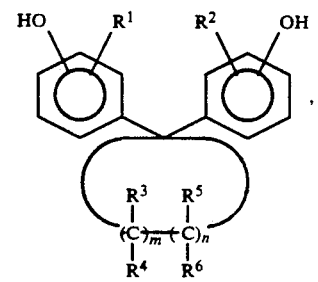

in which each symbol has the same meaning as defined above, to a hydrogenation reaction and a dehydration reaction concurrently in the simultaneous presence of a hydrogenation catalyst and a dehydration catalyst.

Alternatively, the 1,1-dicyclohexyl cycloalkane derivative of the general formula (I) can be prepared by first hydrogenating the 1,1-di(hydroxyphenyl) cycloalkane compound of the general formula (II) to give a 1,1-di(hydroxycyclohexyl) cycloalkane compound represented by the general formula

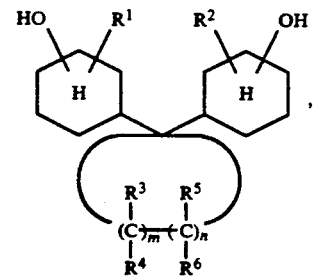

in which each symbol has the same meaning as defined above, and then dehydrating and hydrogenating the compound of the general formula (III).

The traction-drive fluid of the invention comprises at least 1% by weight or, preferably, from 5 to 60% by weight of the 1,1-dicyclohexyl cycloalkane derivative of the general formula (I).

BRIEF DESCRIPTION OF THE DRAWING

FIG. 4 is a graph showing the traction coefficient of the fluids in Examples 1, 4, 5 and 6 and Comparative Example 1 as a function of temperature.

FIGS. 11A and 11B, 12 and 13 are a $^1$H-NMR diagram (solvent: CDCl$_3$), a $^{13}$C-NMR diagram (solvent: CDCl$_3$) and a GC-MS diagram, respectively of 1,1-dicyclohexyl cyclopentane prepared in Example 7.

DETAILED DESCRIPTION OF THE PREFERRED EMBODIMENTS

Figure 1:
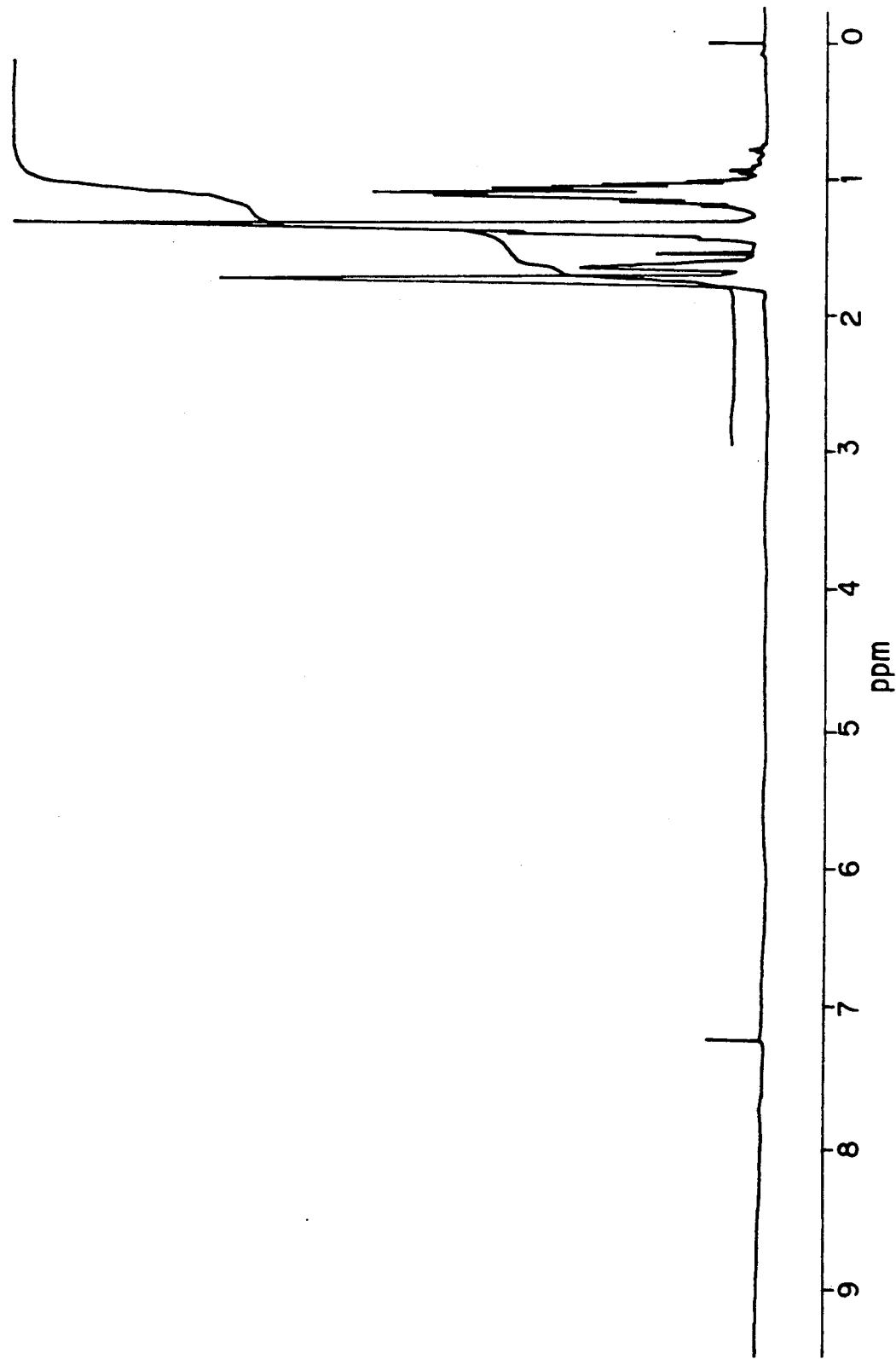
FIGS. 1, 2 and 3 are a $^1$H-NMR diagram (solvent: CDCl$_3$), a $^{13}$C-NMR diagram (solvent: CDCl$_3$) and a GC-MS diagram, respectively, of 1,1-dicyclohexyl cyclohexane prepared in Example 1.

The 1,1-dicyclohexyl cycloalkane derivative represented by the above given general formula (I) is a novel compound not known in the prior art nor described in any literatures.

This novel compound can be synthesized from the 1,1-di(hydroxyphenyl) cycloalkane compound represented by the above given general formula (II) as the starting material Namely, the compound of the general formula (II) is first hydrogenated to give a 1,1-di(hydroxycyclohexyl) cycloalkane compound represented by the above given general formula (III) which is then subjected to a dehydration treatment and hydrogenation treatment to give the compound of the general formula (I).

In the general formulas (I), (II) and (III), each of the symbols $R^1$, $R^2$, $R^3$, $R^4$, $R^5$ and $R^6$ can be a hydrogen atom or a lower alkyl group having 1 to 6 carbon atoms including methyl, ethyl, propyl, isopropyl, butyl, isobutyl, tert-butyl, pentyl and hexyl groups. $R^1$ to $R^6$ can be the same ones or different ones each independently from the others. When a molecule of the compound of the general formula (I) has two or more of each of $R^3$, $R^4$, $R^5$ and $R^6$, they can be the same ones or different ones from each other albeit they are denoted by the same symbol. Assuming that the subscript m is equal to 2, for example, a molecule of the compound has two of the groups denoted by $R^3$ which can be, one, a methyl group and, the other, an ethyl group. Further, each of the groups denoted by $R^3$, $R^4$, $R^5$ and $R^6$ can be a divalent group forming an alkylene group jointly with either one of the other groups. The alkylene group has 1 to 12 carbon atoms and can be straightly linear or branched in structure. Examples of the alkylene group include methylene, ethylene, propylene, trimethylene, isopropylidene and isobutylene groups.

The reaction for the preparation of the compound of the general formula (I) from the compound of the general formula (II) is performed in the presence of hydrogen, a hydrogenation catalyst and a dehydration catalyst. In practice, the reaction can be performed in three different ways. Firstly, the reaction is performed in the simultaneous presence of hydrogen, a hydrogenation catalyst and a dehydration catalyst. Secondly, the compound of the general formula (II) is first hydrogenated by using hydrogen and a hydrogenation catalyst and the hydrogenation product is then subjected to a reaction by using hydrogen, a hydrogenation catalyst and a dehydration catalyst. Thirdly, the compound of the general formula (II) is hydrogenated by using hydrogen and a hydrogenation catalyst to give a hydrogenation product which is subjected to successive reactions first by using a dehydration catalyst and then by using hydrogen and a hydrogenation catalyst to effect the second hydrogenation reaction. Though not limitative, the first method is preferred among the three because the reaction can be completed in one pot to be time-saving.

The hydrogenation catalyst used in the above mentioned reaction can be any one of conventional hydrogenation catalysts containing one or more of the metallic elements such as nickel, ruthenium, palladium, platinum, rhodium, iridium, copper, chromium, molybdenum, cobalt, tungsten and the like. These metallic elements can be used as supported on a suitable catalyst carrier such as active carbon and the like.

The dehydration catalyst is preferably a solid acid catalyst including conventional ones such as, for example, terra abla, i.e. activated earth and acid clay; zeolites, silica gel, alumina gel, silica-alumina gel, cation-exchange resins, heteropolyacids and the like.

In carrying out the reaction according to the inventive method, the hydrogenation catalyst is used in an amount in the range from 0.1 to 100% by weight or, preferably, from 1 to 20% by weight and the solid acid catalyst is used in an amount in the range from 0.1 to 100% by weight or, preferably, from 1 to 20% by weight each based on the amount of the starting material.

If desired, organic solvents can be used as a reaction medium in which the reaction according to the inventive method is performed. Examples of suitable organic solvents include saturated hydrocarbon solvents such as n-pentane, n-hexane, decane, cyclopentane, cyclohexane, methyl cyclohexane, ethyl cyclohexane, decahydronaphthalene and the like, aromatic hydrocarbon solvents such as benzene, toluene, xylene, tetrahydronaphthalene and the like and polar organic solvents such as acetone, ethyl alcohol and the like, of which the saturated hydrocarbon solvents are preferred because the aromatic hydrocarbon solvents may be hydrogenated in their part and the polar solvents can also be hydrogenated or dehydrated as a possibility The above mentioned reaction is performed at a temperature in the range from room temperature to 300° C. or, preferably, from room temperature to 220° C. under a pressure in the range from normal pressure to 200 kg/cm$^2$G or, preferably, from 5 to 150 kg/cm$^2$G. The reaction is complete usually within 0.5 to 24 hours or, in most cases, within 1 to 8 hours. A good efficiency of the reaction can be obtained by first hydrogenating the starting compound at about 120° C. for about 2 hours and then dehydrating and hydrogenating the product in the first step reaction at a temperature of 180° to 200° C. for about 2 hours. The above mentioned temperature range is important because the dehydration reaction can hardly proceed at a temperature lower than room temperature while the starting compound of the general formula (II) may be subject to thermal decomposition when the temperature exceeds the upper limit. After completion of the reaction, the reaction mixture is filtered to remove the solid catalysts and, if necessary, stripped to be freed from the solvent to give the desired 1,1-dicylohexyl cycloalkane compound of the general formula (I) as the product.

Examples of the 1,1-dicyclohexyl cycloalkane derivative represented by the general formula (I) and synthesized by the above described method include: 1,1-dicyclohexyl cyclopentane; 1-cyclohexyl-1-(methyl cyclohexyl) cyclopentanes; 1-cyclohexyl-1-(ethyl cyclohexyl) cyclopentanes; 1-cyclohexyl-1-(propyl cyclohexyl) cyclopentanes; 1-cyclohexyl-1-(butyl cyclohexyl) cyclopentanes; 1,1-di(methyl cyclohexyl) cyclopentanes; 1-(methyl cyclohexyl)-1-(ethyl cyclohexyl) cyclopentanes; 1,1-di(ethyl cyclohexyl) cyclopentanes; 1,1-dicyclohexyl-(methyl cyclopentanes); 1-cyclohexyl-1-(methyl cyclohexyl)-(methyl cyclopentanes); 1-cyclohexyl-1-(ethyl cyclohexyl)-(methyl cyclopentanes); 1-cyclohexyl-1-(methyl cyclohexyl)-(ethyl cyclopentanes); 1,1-di(methyl cyclohexyl)-(methyl cyclopentanes); 1,1-dicyclohexyl-(dimethyl cyclopentanes); 1,1-dicyclohexyl(methyl ethyl cyclopentanes); 1,1-dicyclohexyl cyclohexane; 1-cyclohexyl-1-(methyl cyclohexyl)-cyclohexanes; 1-cyclohexyl-1-(ethyl cyclohexyl) cyclohexanes; 1-cyclohexyl-1-(propyl cyclohexyl) cyclohexanes; 1-cyclohexyl-1-(butyl cyclohexyl) cyclohexanes; 1,1-di(methyl cyclohexyl) cyclohexanes; 1-(methyl cyclohexyl)-1-(ethyl cyclohexyl) cyclohexanes; 1,1-di(ethyl cyclohexyl) cyclohexanes; 1,1-dicyclohexyl-(methyl cyclohexanes); 1-cyclohexyl-1-(methyl cyclohexyl)-(methyl cyclohexanes); 1-cyclohexyl-1-(ethyl cyclohexyl)-(methyl cyclohexanes); 1-cyclohexyl-1-(methyl cyclohexyl)-(ethyl cyclohexanes); 1,1-di(methyl cyclohexyl)-(methyl cyclohexanes); 1,1-dicyclohexyl-(dimethyl cyclohexanes); 1,1-dicyclohexyl-(methyl ethyl cyclohexanes); 2,2-dicyclohexyl-[2.2.1]bicycloheptane; 2-cyclohexyl-2-(methyl cyclohexyl)-[2.2.1]bicycloheptanes; 2,2-di(methyl cyclohexyl)[2.2.1]bicycloheptanes; 2,2-dicyclohexyl-1,7,7-trimethyl[2.2.1]bicycloheptane; 8,8-dicyclohexyl-[4.3.0] bicyclononane; 2,2-dicyclohexyl-[2.2.2] bicyclooctane and the like.

These 1,1-dicyclohexyl cycloalkane derivatives in general have a low viscosity and a high traction coefficient at high temperatures so that they are quite satsifactory as a constituent of a traction-drive fluid. In addition, the 1,1-dicyclohexyl cycloalkane derivative can be used as blended with other conventional traction-drive fluids to improve the performance thereof. When the inventive compound is used as blended with other fluids, the content thereof in the traction-drive fluid should be at least 1% by weight or, preferably, in the range from 5 to 60% by weight. By this means of blending with the inventive 1,1-dicyclohexyl cycloalkane compound, a conventional traction-drive fluid can be imparted with a remarkably improved traction coefficient. Since the inventive 1,1-dicyclohexyl cycloalkane compound has a lower viscosity than that of conventional traction-drive fluids, the traction coefficient of the blend can be increased by increasing the proportion of the inventive compound in the blend.

In the following, examples are given to illustrate the present invention in more detail.

EXAMPLE 1

Into an autoclave of 1 liter capacity were introduced 101.79 g of 1,1-bis(4-hydroxyphenyl) cyclohexane (Bisphenol Z, a product by Honshu Chemical Co., Ltd.) 30.40 g of a hydrogenation catalyst containing 5% by weight of ruthenium supported on an active carbon (a product by N.E Chemicat Co., Ltd.), 50.40 g of an activated earth (Galleon Earth NS, a product by Mizusawa Chemical Co., Ltd.) and 500 ml of ethyl cyclohexane as a solvent to form a reaction mixture which was heated at a temperature of 120° C. for 2 hours and then at 190° C. for 2 hours under a hydrogen pressure of 75 kg/cm$^2$G to effect the reaction. After the end of the above mentioned reaction time, the reaction mixture cooled to room temperature and taken out of the autoclave was filtered to remove the catalyst and the filtrate was freed from the solvent by distillation. The thus obtained reaction product was analyzed by the $^1$H-NMR method to find no peaks assignable to the aromatic structure or olefinic unsaturation indicating at least 99.9% of hydrogenation. Further, the analysis by the $^{13}$C-NMR method indicated presence of a single quaternary carbon atom and two tertiary carbon atoms, the rest being secondary carbon atoms, in a molecule. The molecular weight of the compound was 248 corresponding to a molecular formula of $C_{18}H_{32}$ according to the result of the GC-MS analysis. The gas-chromatographic (FID) diagram had a single peak with a retention time of 15.1 minutes showing complete absence of the starting material. The gas chromatographic analysis was conducted under the following conditions.

Column: OV-7, stainless steel column, 2 meters.

Column temperature: 80° C. to 330° C., increased at a rate of 10° C./minute.

Temperature at the injection port: 350° C.

Carrier gas: nitrogen, 45 ml/minute

Detector: FID.

Figure 2:
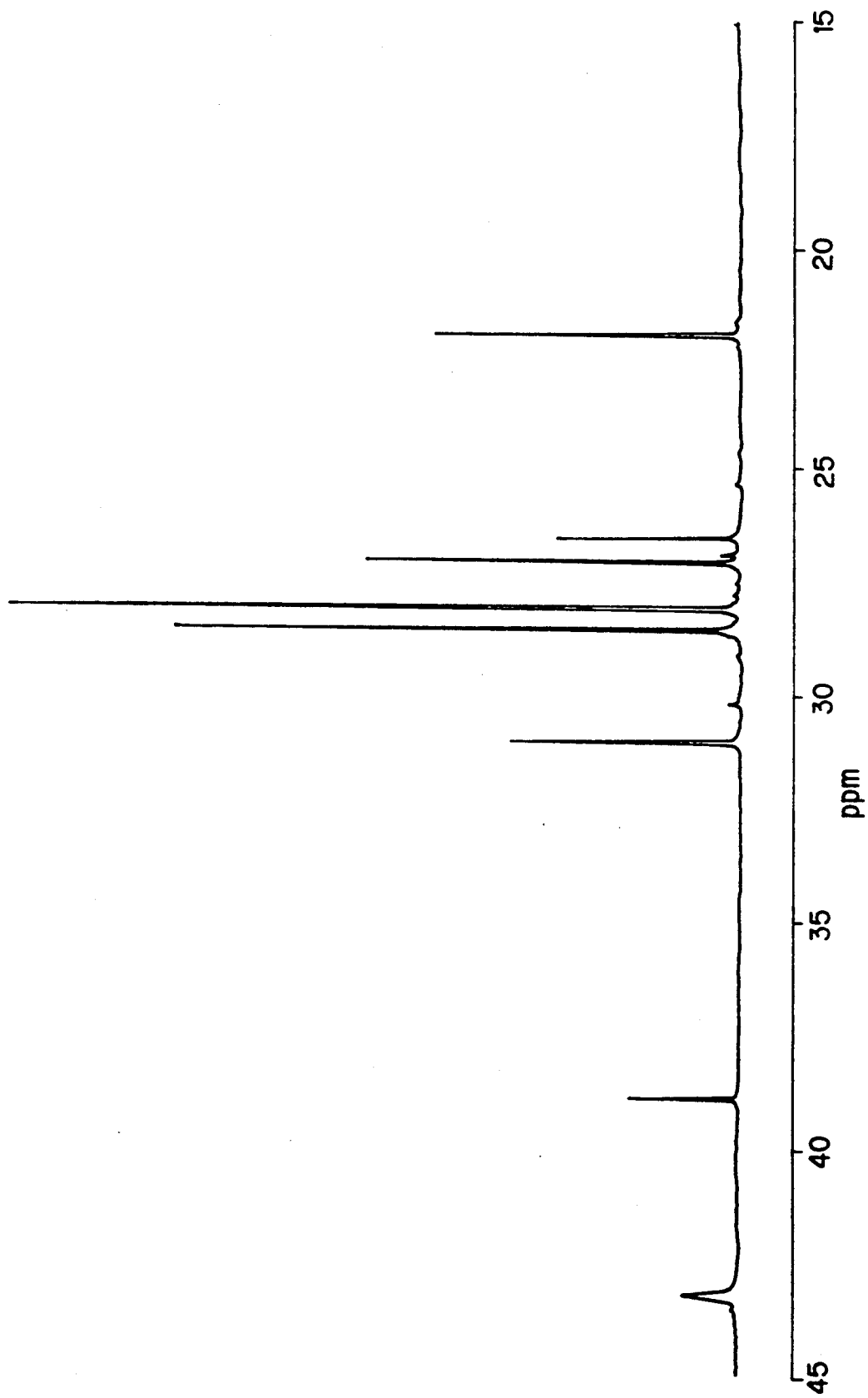
Figure 3:
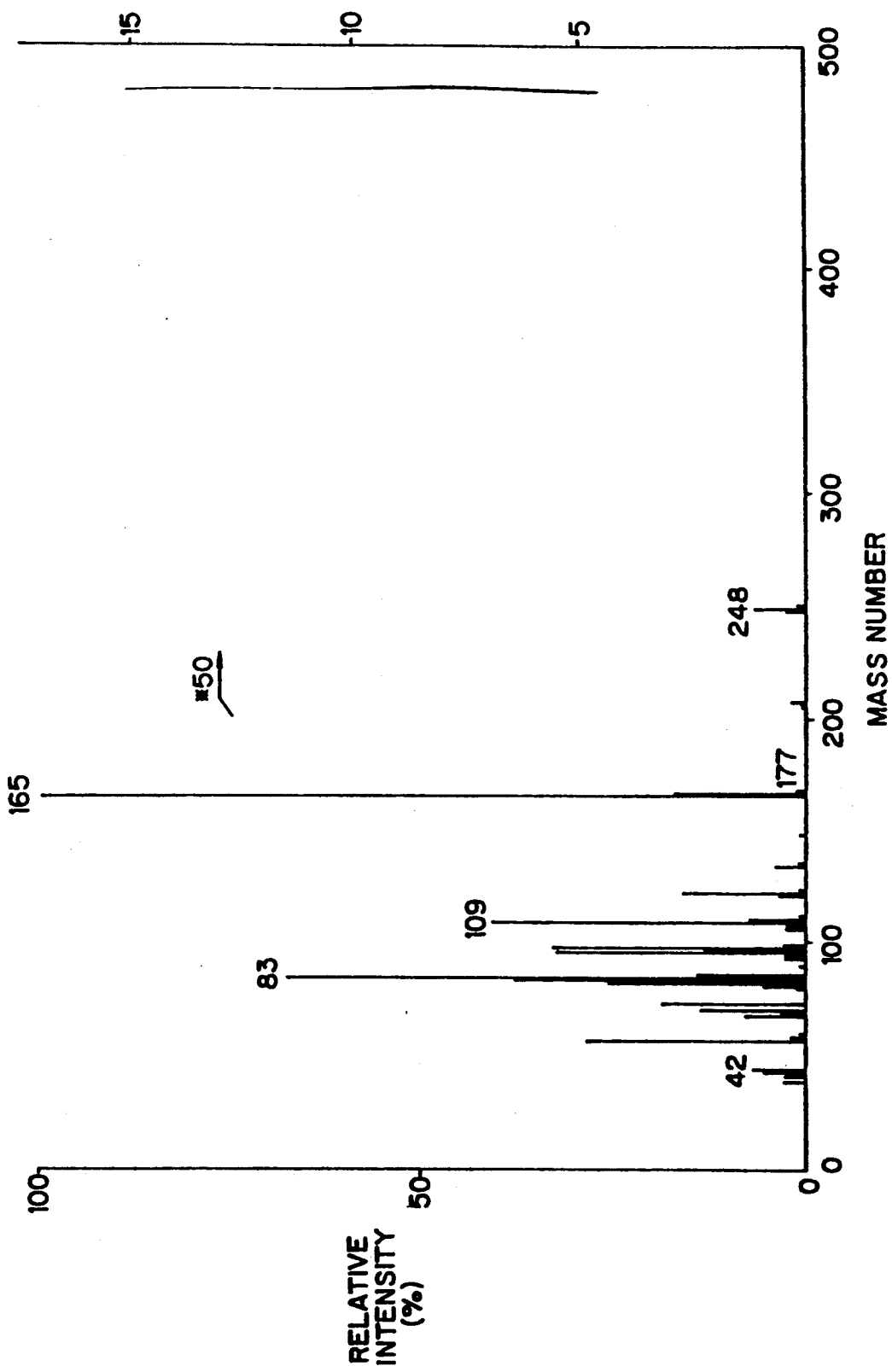

The above given analytical results supported the conclusion that the product could be identified to be 1,1-dicyclohexyl cyclohexane. FIGS. 1, 2 and 3 of the accompanying drawing show a $^1$H-NMR diagram, $^{13}$C-NMR diagram and GC-MS diagram, respectively, of the compound. This compound had following physical properties.

Kinematic viscosity: 34.24 centistokes at 40° C.; 4.399 centistokes at 100° C.

Viscosity index: −50.

Specific gravity (15/4° C.): 0.9583.

Refractive index $n_D^{20}$: 1.5131.

Further, the traction coefficient of this compound was determined in a temperature range from 40° C. to 140° C. using a double-cylinder friction tester to give the results graphically shown in FIG. 4. The two-disk machine had two cylinders of the same size with a diameter of 52 mm and thickness of 6 mm in contact with each other and the peripheral side surface of the driven cylinder was bulged in a barrel-like form with a radius of curvature of 10 mm while the driving cylinder had a flat peripheral side surface without crowning. While the two cylinders were contacted with a load of 7 kg given by a spring, they were rotated, one, at a constant velocity of 1500 rpm and, the other, at a continuously varied velocity of 1500 to 1750 rpm to determine the tangential force, i.e. traction force, from which the traction coefficient was calculated. Each of the cylinders was made from a bearing steel SUJ-2 having a mirror-polished surface and the maximum Hertzian contact pressure was 112 kgf/mm$^2$.

FIG. 4 gives the traction coefficient determined at a slip factor of 5% as a function of the oil temperature which was varied in the range from 40° C. to 140° C. by heating the oil tank with a heater.

EXAMPLE 2

The same synthetic reaction as in Example 1 was undertaken except that the reaction temperature was 190° C. throughout the reaction time of 4 hours. The reaction product was analyzed by the gas chromatography (FID) to give the same peak as in Example 1 though with a selectivity of 90%.

EXAMPLE 3

Into an autoclave of 1 liter capacity were introduced 200 g of Bisphenol Z, 30.28 g of the same ruthenium catalyst for hydrogenation as used in Example 1 and 400 ml of acetone as a solvent to form a reaction mixture which was heated at a temperature of 130° C. for 3 hours under a hydrogen pressure of 75 kg/cm$^2$G to effect the hydrogenation reaction. After the end of the above mentioned reaction time, the reaction mixture cooled to room temperature and taken out of the autoclave was filtered to remove the catalyst. Analysis of the filtrate indicated that the acetone used as the solvent had been completely converted into isopropyl alcohol. Gas chromatographic analysis (FID) of the filtrate gave three peaks in the diagram of which the first of about 5% fraction was the same peak as obtained in Example 1 and the second peak at the retention time of 17.5 minutes and the third peak at the retention time of 20.8 minutes corresponded to an about 15% fraction and about 80% fraction, solvent from the filtrate by distillation was a solid which was recrystallized from hexane to give 135 g of a product having a retention time of 20.8 minutes in the gas chromatography with a purity of 98%. This product could be identified to be 1,1-bis(4-hydroxycyclohexyl) cyclohexane from the results of the $^1$H-NMR analysis, 13C-NMR analysis and GC-MS analysis In the next place, 109.56 g of the above obtained 1,1-bis(4-hydroxycyclohexyl) cyclohexane, 30.40 g of the same hydrogenation catalyst as used above, 50.40 g of an activated earth and 500 ml of ethyl cyclohexane as a solvent were introduced into the same autoclave of 1 liter capacity as used above and heated at a temperature of 195° C. for 3 hours under a hydrogen pressure of 60 kg/cm$^2$G to effect the reaction After the end of the reaction time, the reaction mixture cooled to room temperature and taken out of the autoclave was filtered to remove the catalyst and the filtrate was analyzed by the gas chromatography (FID) to find that the gas chromatogram had the same peak with a retention time of 15.1 minutes as obtained in Example 1 in a selectivity of 95% with complete disappearance of the peak with a retention time of 20.8 minutes.

COMPARATIVE EXAMPLE 1

Into a four-necked flask of 2 liter capacity were introduced 522 g of toluene, 27.6 g of anhydrous aluminum chloride and 12.6 g of nitromethane to form a mixture and 181.2 g of methallyl chloride were added dropwise to the mixture under agitation at 10° C. over a period of 2 hours followed by further continued agitation for additional 1 hour to complete the reaction. Thereafter, 75 ml of water were added to the reaction mixture to decompose the aluminum chloride and the organic phase taken by phase separation was washed once with 200 ml of water and twice with 300 ml of a 1N aqueous solution of sodium hydroxide followed by dehydration over anhydrous magnesium sulfate. Thereafter, the mixture was stripped of the unreacted starting materials on a rotary evaporator and subjected to distillation under reduced pressure to give 262.5 g of a fraction boiling at 110° to 115° C. under a pressure of 0.12 mmHg. Analysis of this product indicated that the product was composed of 75% of 2-methyl-1,2-ditolyl propane and 25% of 2-methyl-1,1-ditolyl propane as an isomerization product of the former.

In the next place, 250 g of the above obtained product were introduced into an autoclave of 1 liter capacity together with 20 g of a nickel catalyst (N-113, a product by Nikki Chemical Co., Ltd.) and subjected to a hydrogenation reaction at a temperature of 170° C. for 6 hours under a hydrogen pressure of 85 kg/cm$^2$G. After the end of the reaction time, the reaction mixture cooled to room temperature and taken out of the autoclave was filtered to remove the catalyst and the filtrate was analyzed to find that it was composed of 75% of 2-methyl-1,2-di(methyl cyclohexyl) propane and 25% of 2-methyl-1,1-di(methyl cyclohexyl) propane with at least 99.9% hydrogenation of the starting compounds. This product had following physical properties.

Kinematic viscosity: 14.84 centistokes at 40° C.; 2.844 centistokes at 100° C.

Viscosity index: −22.

Specific gravity (15/4° C.): 0.8860.

Refractive index $n_D^{20}$: 1.4813.

Further, the traction coefficient of this product was determined in the same manner as in Example 1 to give the result shown in FIG. 4 as a function of temperature.

EXAMPLE 4

The fluid obtained in Comparative Example 1 described above was blended with 1,1-dicyclohexyl cyclohexane obtained in Example 1 in a weight ratio of 1:1 and the traction coefficient of the blend was determined in the same manner as in Example 1 to give the result shown in FIG. 4 as a function of temperature. This blended fluid had following physical properties.

Kinematic viscosity: 20.96 centistokes at 40° C.; 3.456 centistokes at 100° C.

Viscosity index: −30.

Specific gravity (15/4° C.): 0.9199.

Refractive index $n_D^{20}$: 1.4961.

EXAMPLE 5

Into a flask of 1 liter capacity with a separable cover equipped with a gas inlet tube, stirrer and thermometer were introduced 102.57 g of cyclohexanone, 76.65 g of phenol, 186.27 g of o-cresol and 8 ml of thioglycolic acid to form a reaction mixture, into which hydrogen chloride gas was blown at 54° C. for 3 hours under agitation to effect the reaction. Thereupon, the reaction mixture was converted into a solid of violet in color. Then, blowing of the hydrogen chloride gas was interrupted and the solid in the flask was admixed with 200 ml of p-xylene and 200 ml of hot water at 70° to 80° C. followed by agitation at 70° C. for 1 hour so that the solid was disintegrated into pink-colored crystals which were collected by filtration with suction after cooling to room temperature. The crystals were recrystallized from a 20:1 mixture of toluene and ethyl alcohol to give 235 g of white crystals with a pale tint of violet. The crystals were dissolved in acetone and the solution was analyzed by the gas chromatography (FID) to give three constituents, referred to as the compounds (a), (b) and (c) hereinbelow, in a relative amount of 10:22:68 at the retention times of 8.1 minutes, 8.6 minutes and 9.0 minutes, respectively.

Column: OV-101 (capillary), 50 meters.
Column Temperature: 280° C. to 300° C., increased at a rate of 2° C./minute .
Temperature at the injection port: 350° C.
Carrier gas: nitrogen, 60 ml/minute.
Detector: FID.

The results of the $^1$H-NMR, $^{13}$C-NMR and GC-MS analyses of these three compounds making comparison with the analytical results obtained with a standard sample of Bisphenol Z indicated that the compound (a) was Bisphenol Z, compound (b) was a cyclohexane compound substituted at the 1-position with each one molecule of phenol and o-cresol and compound (c) was a cyclohexane compound substituted at the 1-position with two molecules of o-cresol.

Figure 5A:
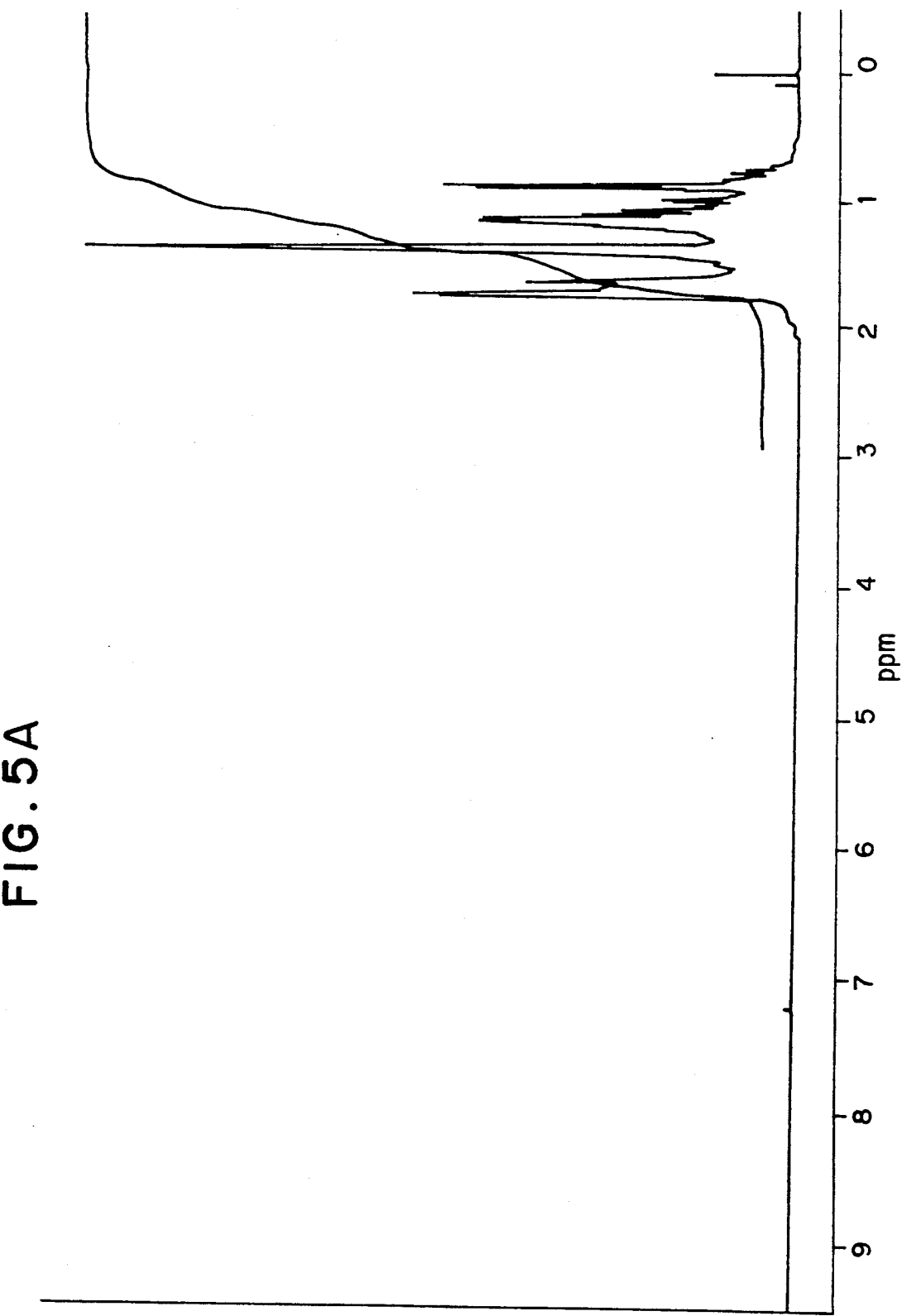
FIGS. 5A and 5B, 6 and 7 are a $^1$H-NMR diagram (solvent CDCl$_3$), a $^{13}$C-NMR diagram (solvent CDCl$_3$) and a GC-MS diagram, respectively, of 1-cyclohexyl-1-(3-methyl cyclohexyl) cyclohexane prepared in Example 5.
Figure 5B:
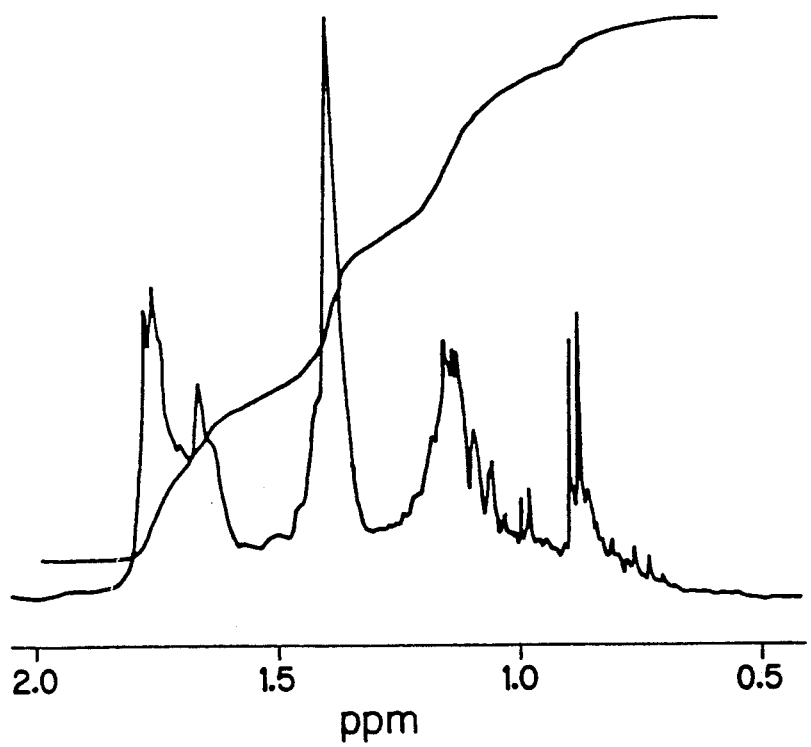
Figure 6:
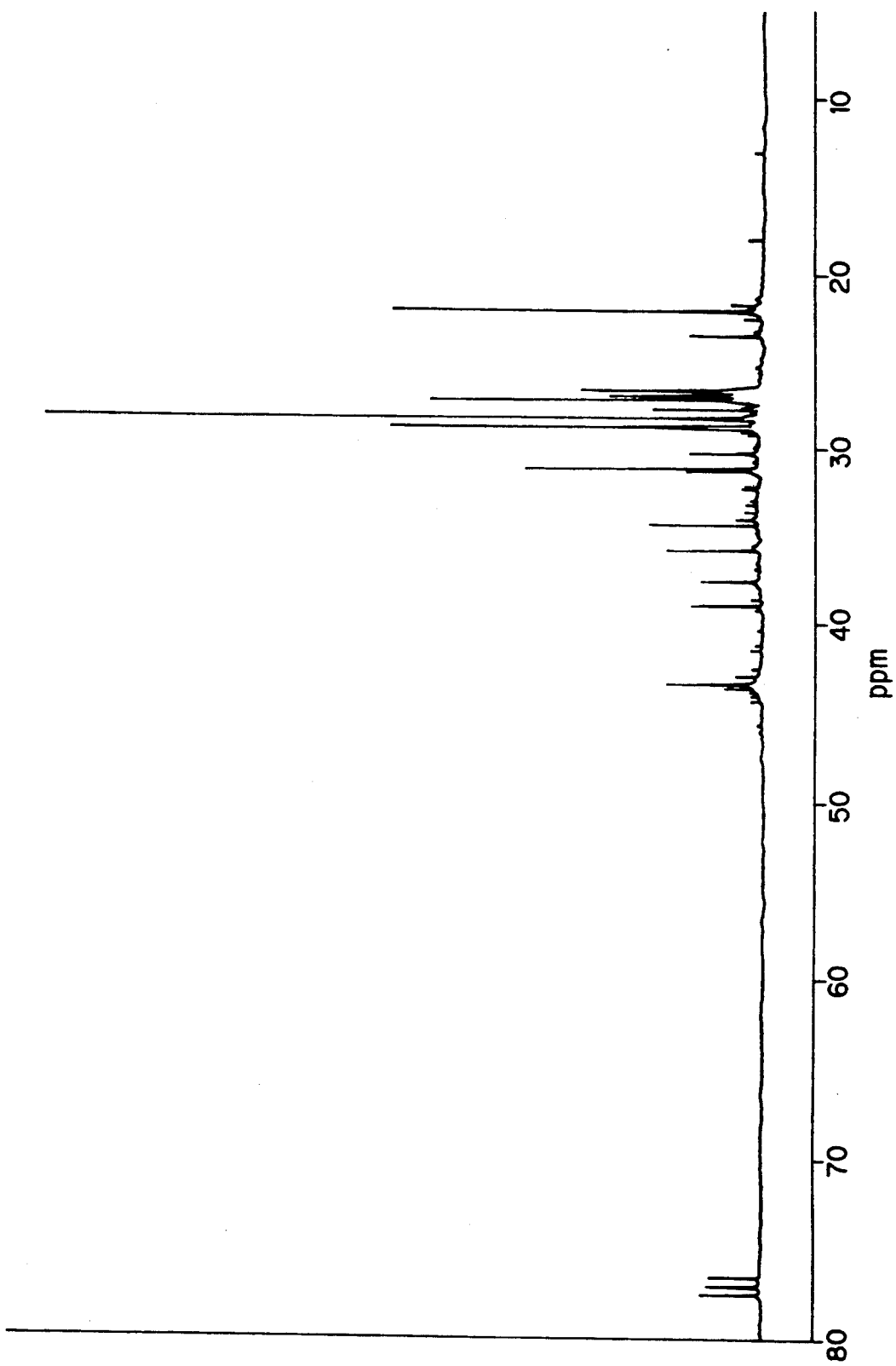
Figure 7:
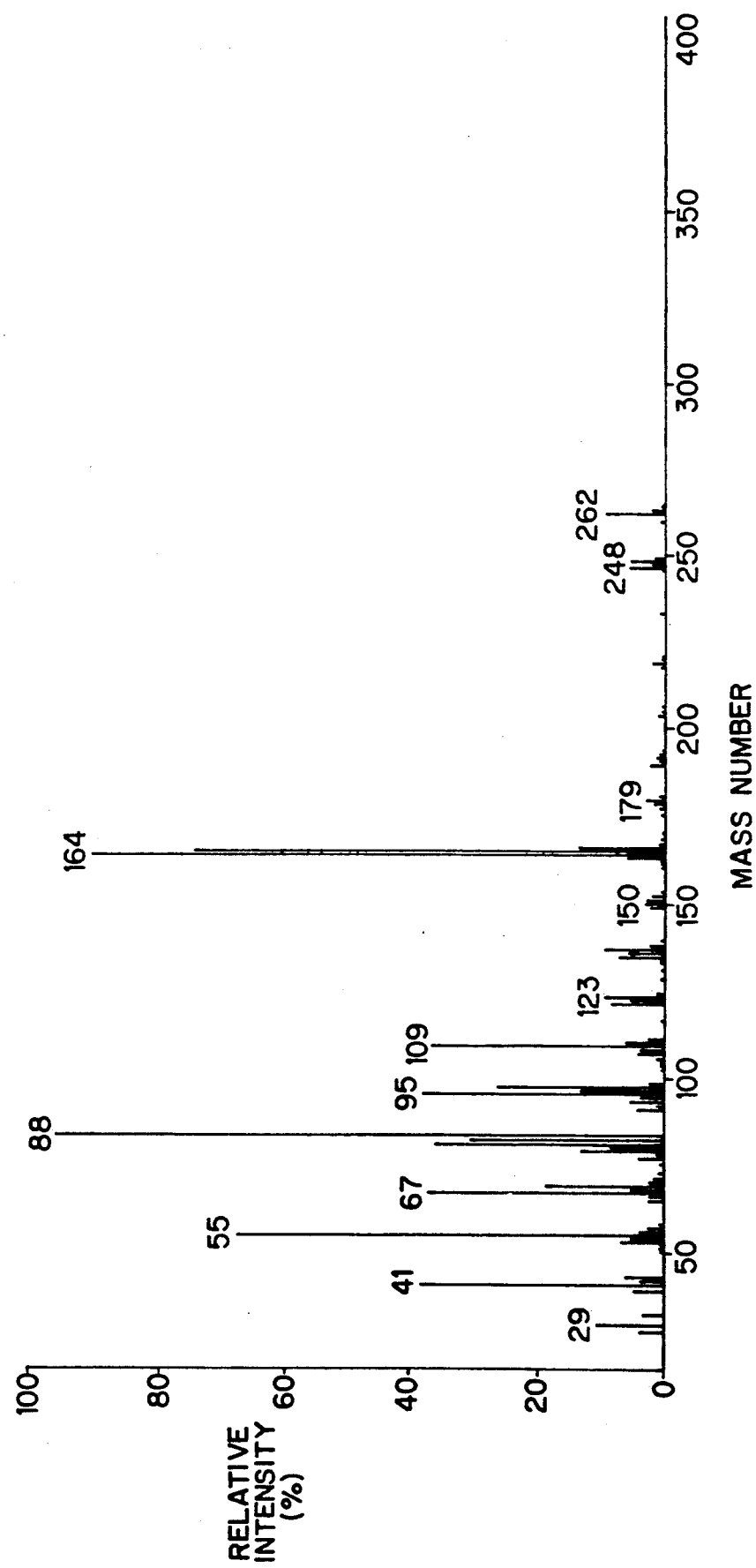

In the next place, 180 g of the thus obtained crystals were introduced into an autoclave of 1 liter capacity together with 15.2 g of the same ruthenium-containing hydrogenation catalyst as used in Example 1, 25.4 g of a USY-type zeolite (HSZ-330HUA, a product by Tosoh Corp.) and 400 ml of dioxane as a solvent to form a reaction mixture which was heated at 120° C. for 2 hours and then at 210° C. for 5 hours under a hydrogen pressure of 75 kg/cm$^2$G to effect the hydrogenation reaction. After completion of the reaction, the reaction product was treated in the same manner as in Example 1 and subjected to analysis to find that the hydrogenation was 99.9% or higher with complete disappearance of the hydroxy groups. Further, the results of the gas chromatographic analysis (FID) and GC-MS analysis indicated that this product was composed of 9% of 1,1-dicyclohexyl cyclohexane C18H32, 24% of 1-cyclohexyl-1-(3-methyl cyclohexyl) cyclohexane C19H34 and 67% of 1,1-di(3-methyl cyclohexyl) cyclohexane C$_{20}$H$_{36}$. The yield of the product was 118 g. FIGS. 5, 6 and 7 show a $^1$H-NMR diagram, $^{13}$C-NMR diagram and GC-MS diagram of the fraction of C$_{19}$H$_{34}$ taken by the liquid chromatography of this product. The above obtained crystalline product as a whole had following physical properties.

Kinematic viscosity: 43.63 centistokes at 40° C.; 4.654 centistokes at 100° C.
Viscosity index: −101.
Specific gravity (15/4° C.): 0.9403.
Refractive index n$_D^{20}$: 1.5048.

Further, FIG. 4 shows the traction coefficient of this product as a function of temperature in the range from 40° C. to 140° C.

EXAMPLE 6

Into a flask of 1 liter capacity with a separable cover equipped with a stirrer and thermometer were introduced 101.24 g of cyclohexanone, 273.76 g of o-cresol, 111.98 g of 35% concentrated hydrochloric acid and 8 ml of thioglycolic acid to form a reaction mixture which was agitated at 60° C. for 1.5 hours so that the reaction mixture was partly solidified to give a slurry. This slurried reaction mixture was then admixed with 300 ml of water and 300 ml of dioxane and further agitated at 80° C. for 1 hour. Thereafter, 20 g of sodium chloride were added thereto so that the mixture was separated into two layers of which the organic phase was taken by phase separation and washed twice with 200 ml of water. Thereafter, this organic solution was freed from volatile matters to precipitate crystals which were recrystallized from a 20:1 mixture of toluene and ethyl alcohol to give 184 g of white crystals The results of the $^1$H-NMR analysis, $^{13}$C-NMR analysis and GC-MS analysis indicated that this crystalline product was composed of a single compound which could be identified to be 1,1-bis(4-hydroxy-3-methyl phenyl) cyclohexane, i.e. the same compound as the compound (c) obtained in Example 5.

Figure 8A:
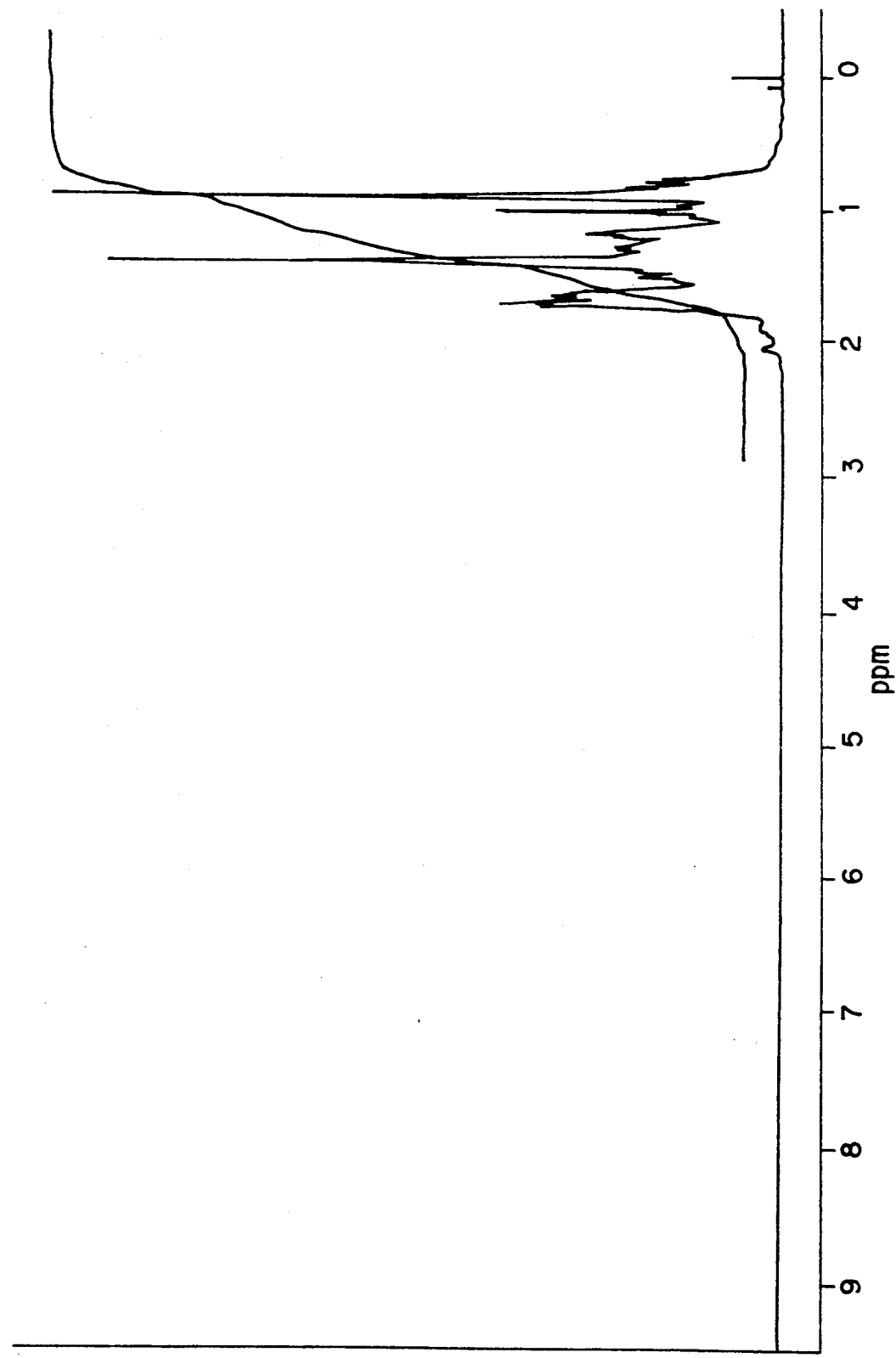
FIGS. 8A and 8B, 9 and 10A and 10B are a $^1$H-NMR diagram (solvent CDCl$_3$), a $^{13}$C-NMR diagram (solvent CDCl$_3$) and a GC-MS diagram, respectively of 1,1-di(3-methyl cyclohexyl) cyclohexane prepared in Example 6. The coordinates for FIGS. 10A and 10B are the same, but in FIG. 10B the peak heights are shown as ten times that of FIG. 10A.
Figure 8B:
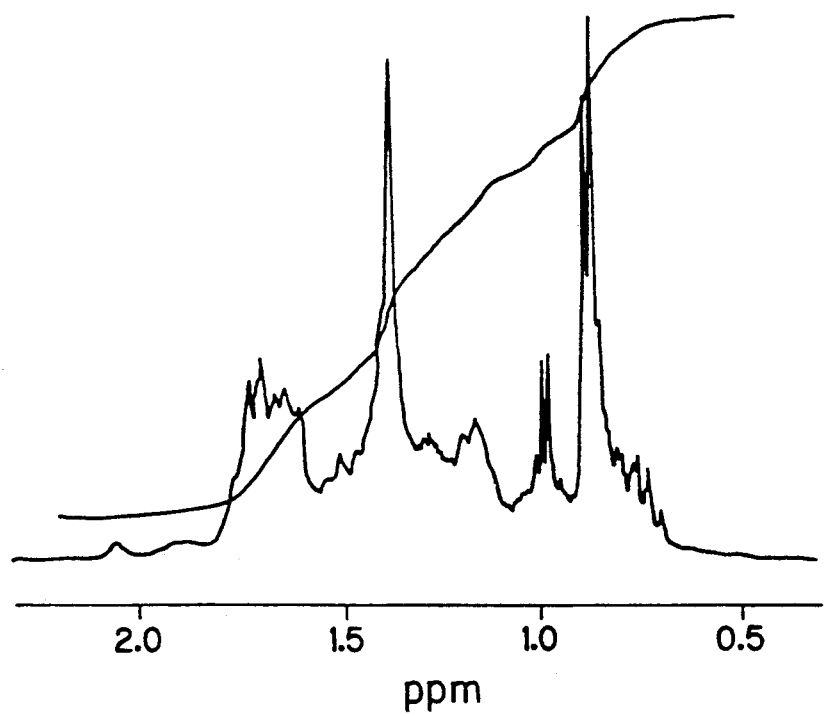
Figure 9:
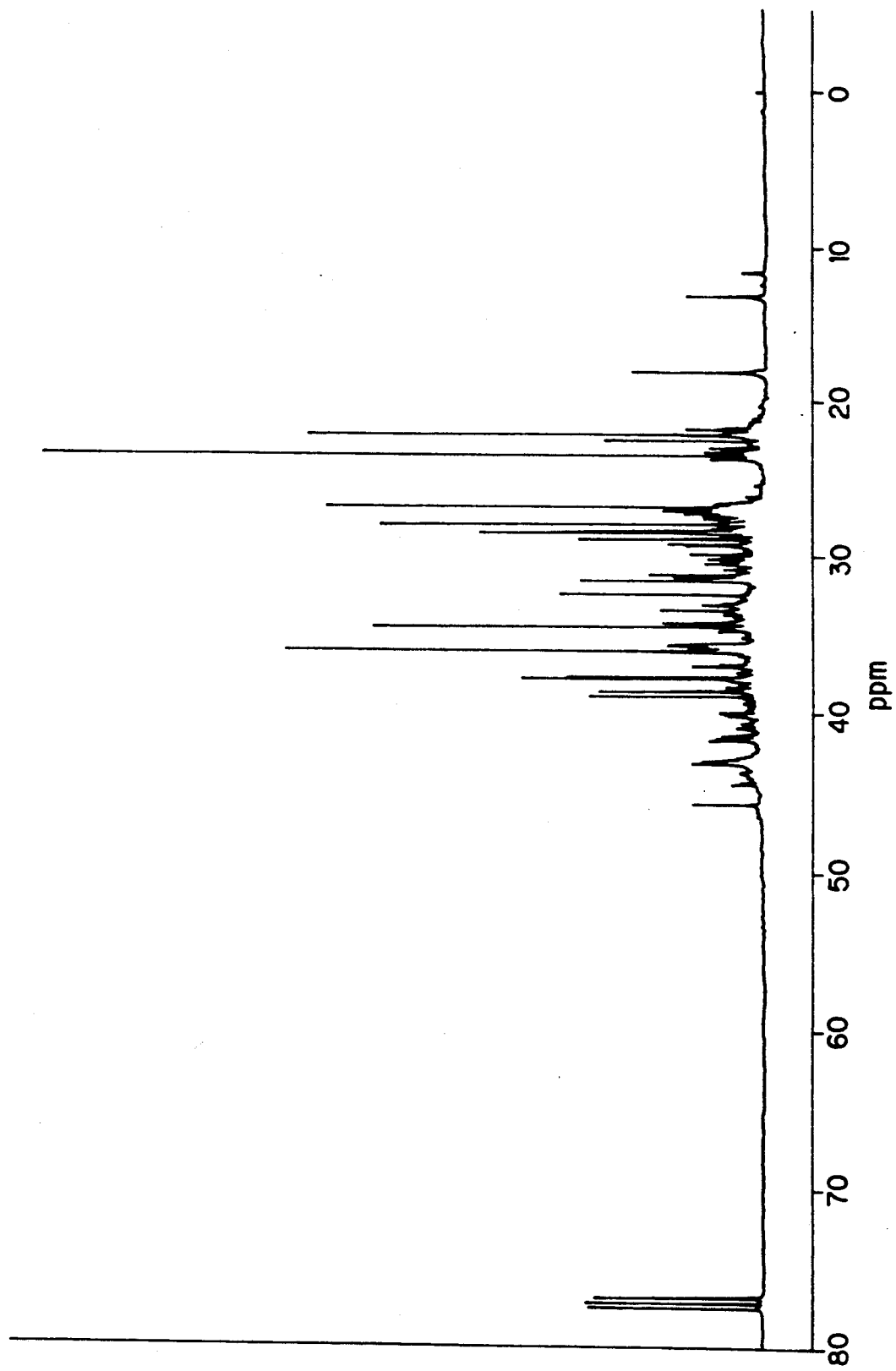
Figure 10A:
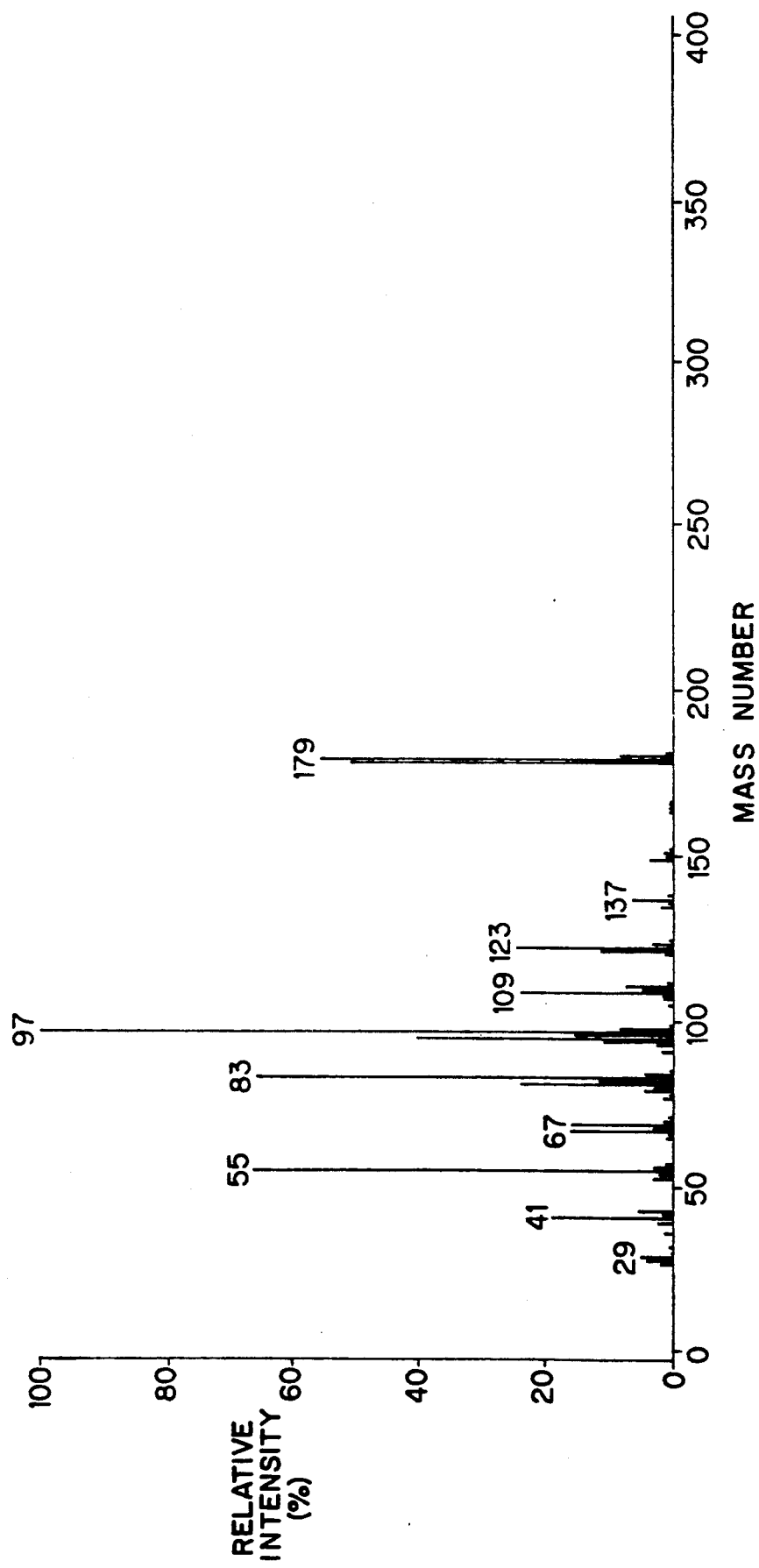
Figure 10B:
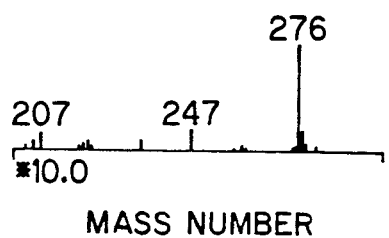

In the next place, 180 g of the thus obtained crystalline product were subjected to the reaction in the same manner as in Example 5. After completion of the reaction, the reaction product was processed in the same manner as in Example 1 and analyzed to find that the hydrogenation was 99.9% or more with complete disappearance of the hydroxy groups. The yield of this product was 148 g. The results of the $^1$H-NMR analysis, $^{13}$C-NMR analysis and GC-MS analysis indicated that this product was 1,1-di(3-methyl cyclohexyl) cyclohexane. FIG. 8, 9 and 10 show diagrams obtained in the $^1$H-NMR, $^{13}$C-NMR and GC-MS analyses, respectively. This product had following physical properties.

Kinematic viscosity: 51.24 centistokes at 40° C.; 4.882 centistokes at 100° C.
Viscosity index: −121
Specific gravity (15/4° C.): 0.9332
Refractive index n$_D^{20}$1.5016

Further, FIG. 4 shows the traction coefficient of this product as a function of temperature in the range from 40° C. to 140° C.

EXAMPLE 7

Into a flask of 1 liter capacity with a separable cover equipped with a stirrer and thermometer were introduced 100.51 g of cyclopentanone, 240.48 g of phenol, 200.00 g of 35% concentrated hydrochloric acid and 16 ml of thioglycolic acid to form a reaction mixture which was agitated at 43° C. for 1 hour followed by standing as such for 24 hours so that the reaction mixture was partly solidified into a slurry-like form. This slurry was filtered with suction and the crystals thus collected were washed successively first with 100 ml of water and then with 100 ml of m-xylene After three times repetition of the procedure of washing, the crystals were dried to give 128.36 g of a white crystalline product The results of the $^1$H-NMR analysis, $^{13}$C-NMR analysis and GC-MS analysis indicated that this crystalline product was composed of a single compound which could be identified to be 1,1-bis(4-hydroxy phenyl) cyclopentane. The gas chromatographic analysis (FID) was conducted under the following conditions. The retention time of this product was 6.6 minutes.

Column: OV-101 (capillary), 50 meters.
Column temperature: 280° C.
Temperature at the injection port: 350° C.
Carrier gas: nitrogen, 60 ml/minute.

In the next place, 120 g of the above obtained crystalline product were introduced into an autoclave of 1 liter capacity together with 20.1 g of the same ruthenium-containing hydrogenation catalyst as used in Example 1, 20.2 g of the same USY-type zeolite as used in Example 5 and 400 ml of dioxane as a solvent and the mixture was heated first at 120° C. for 1 hour and then at 150° C. for 1.5 hours under a hydrogen pressure of 80 kg/cm$^2$G to effect the hydrogenation reaction. Thereafter, the reaction was further continued for additional 4.5 hours by increasing the temperature to 215° C. under an increased hydrogen pressure of 110 kg/cm$^2$G. After completion of the reaction, the reaction mixture was processed in the same manner as in Example 1 to give 108.56 g of a reaction product. The diagram obtained by the $^1$H-NMR analysis indicated complete disappearance of the peaks assignable to the aromatic structure and olefinic unsaturation to give a conclusion that the hydrogenation of the starting compound was at least 99.9%. The result of the $^{13}$C-NMR analysis indicated that the molecule of the product compound had a single quaternary carbon atom and two tertiary carbon atoms, all of the other carbon atoms being secondary. The compound had a molecular weight of 234 corresponding to a molecular formula of $C_{17}H_{30}$ according to the result of the GC-MS analysis. The retention time of the compound in the gas chromatographic analysis (FID) was 4.3 minutes supporting the conclusion that this product was a compound completely different from the starting compound. The above mentioned analytical results led to a conclusion that this product could be identified to be 1,1-dicyclohexyl cyclopentane.

Figure 11A:
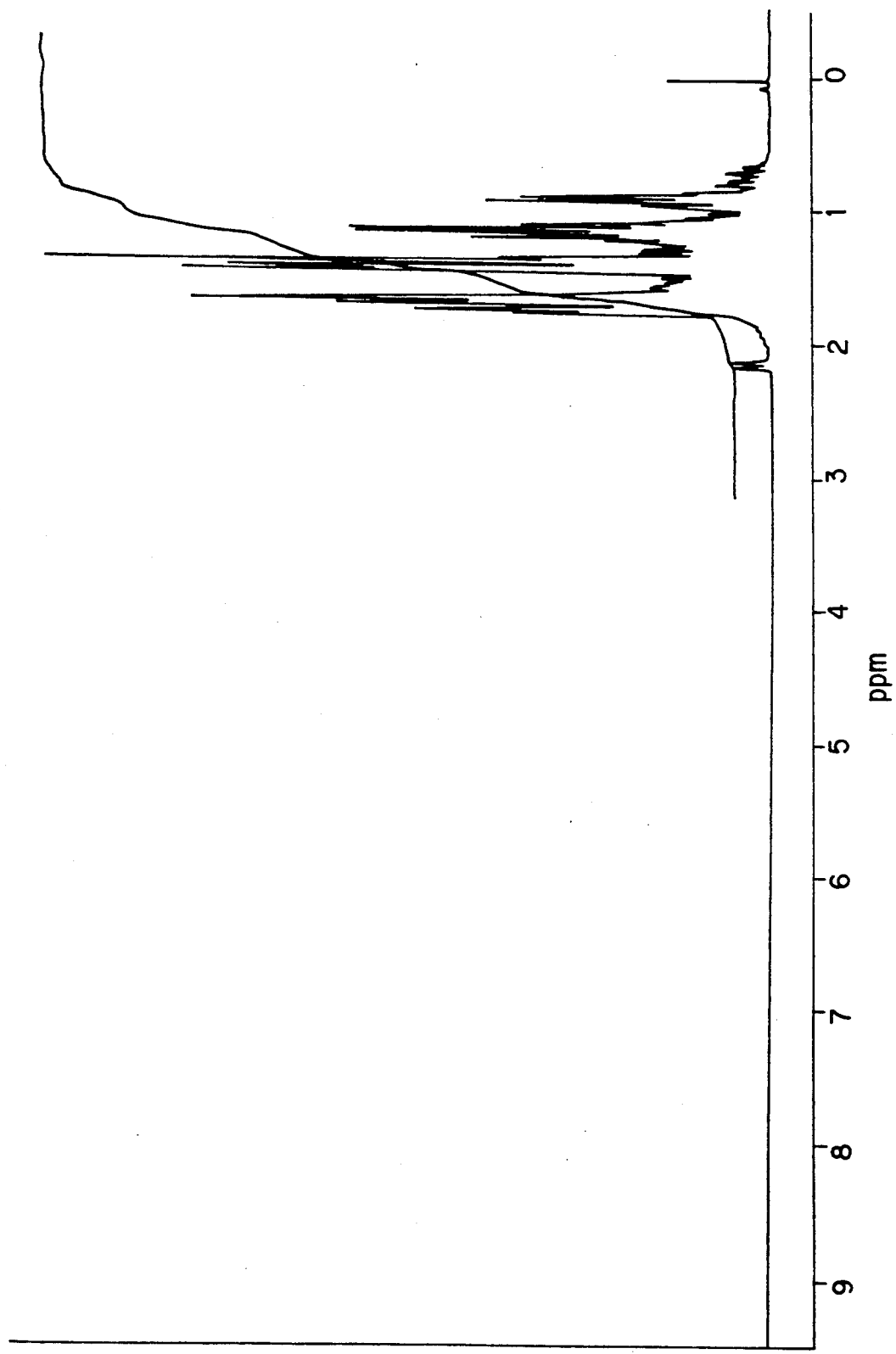
Figure 12:
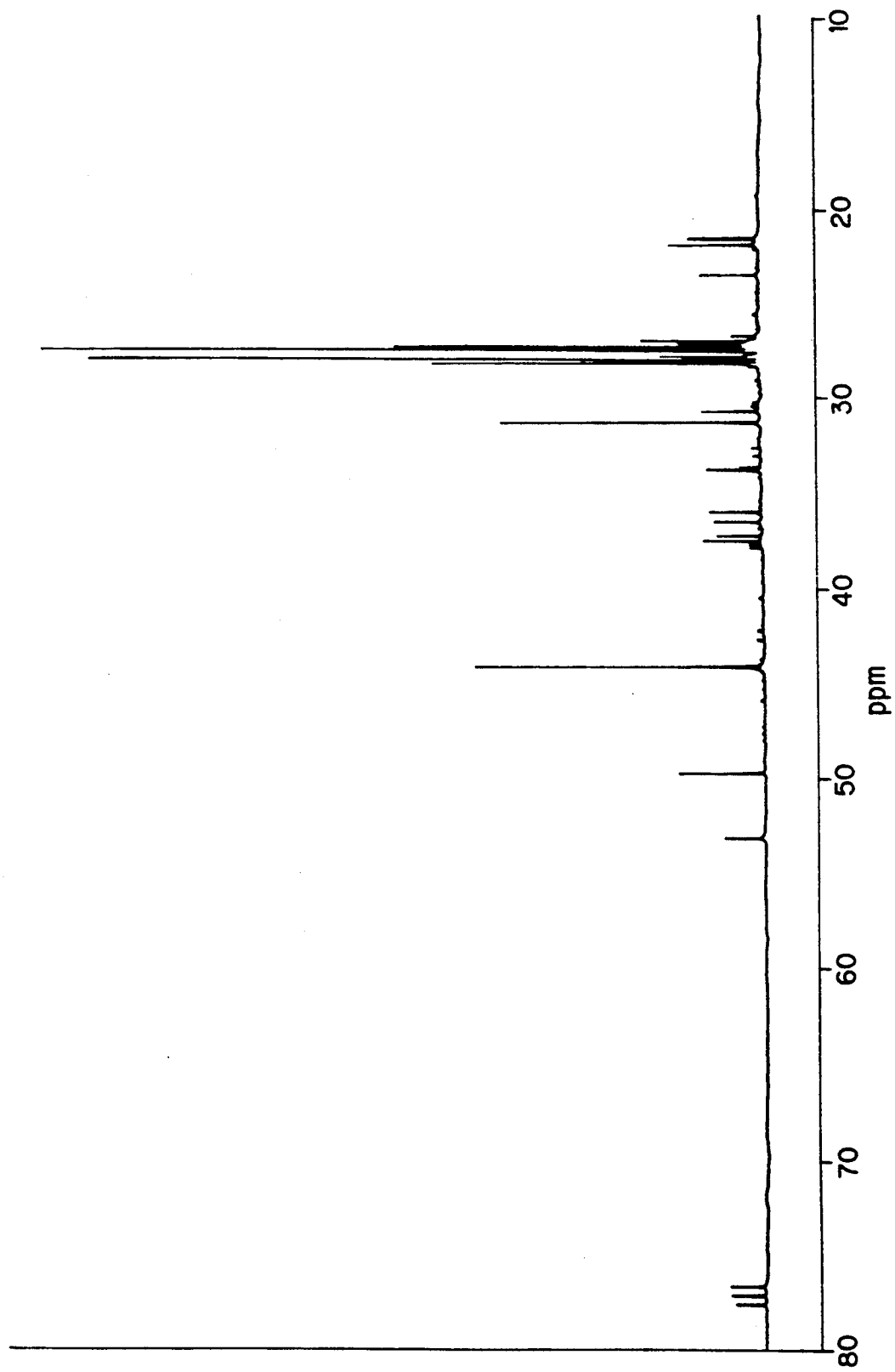
Figure 13:
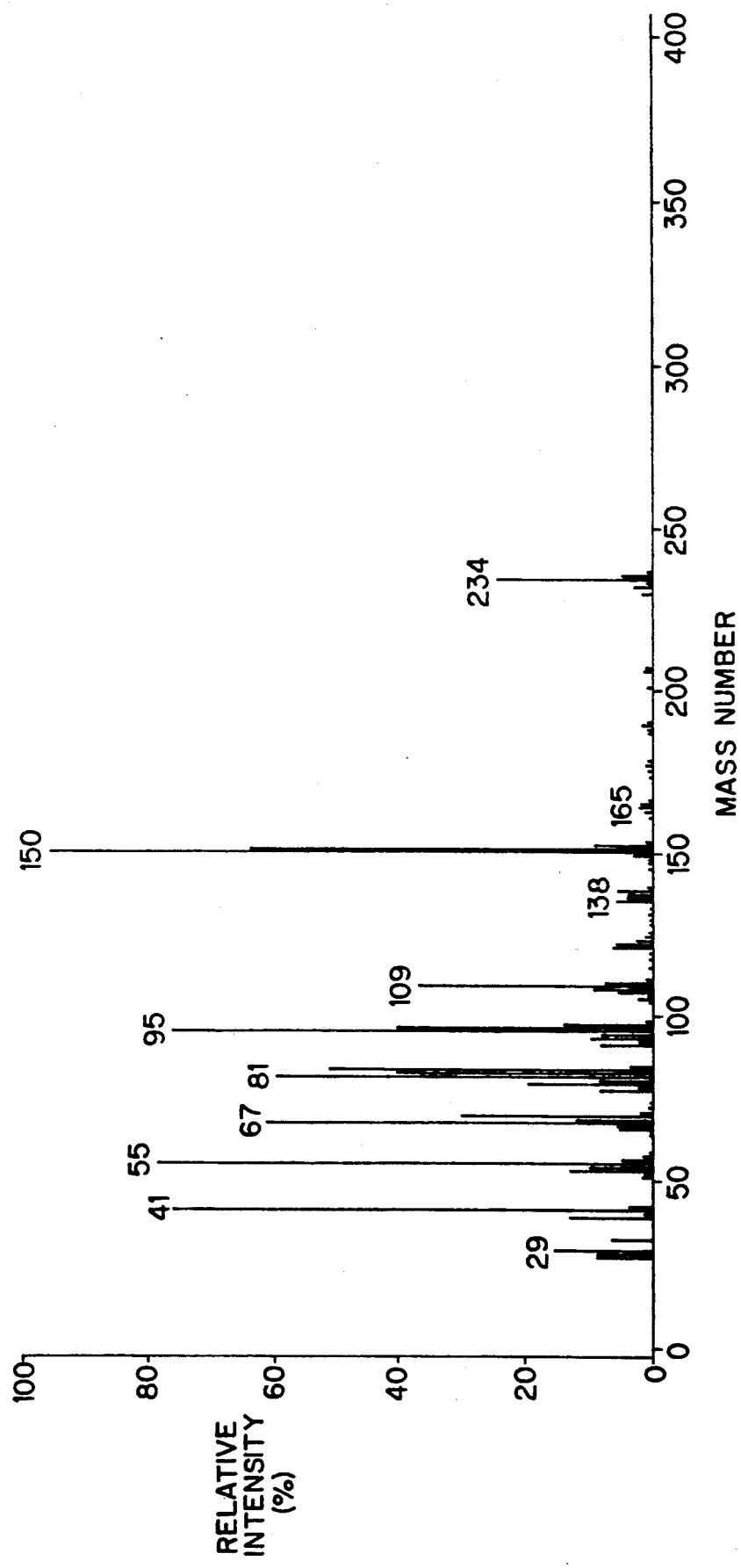

FIGS. 11, 12 and 13 show a $^1$H-NMR diagram, $^{13}$C-NMR diagram and GC-MS diagram, respectively, of this product compound. The compound had following physical properties.

Kinematic viscosity: 25.72 centistokes at 40° C.; 3.788 centistokes at 100° C.
Viscosity index: −53.
Specific gravity (15/4° C.): 0.9586.
Refractive index $n_D^{20}$: 1.5111.

Figure 14:
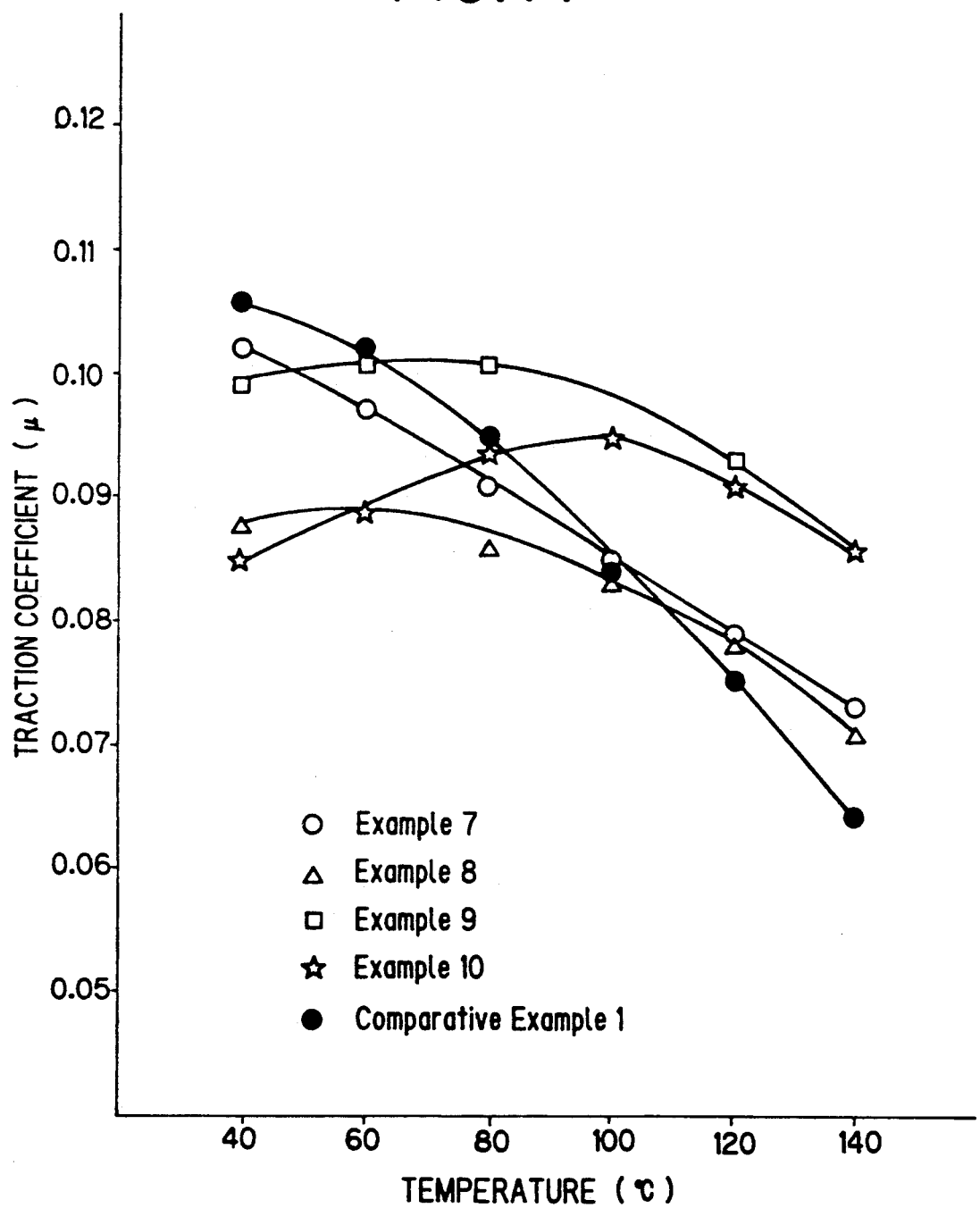
FIG. 14 is a graph showing the traction coefficient of the fluids in Examples 7, 8, 9 and 10 and Comparative Example 1 as a function of temperature.

Further, the traction coefficient of this product compound was determined in the same manner as in Example 1 to give the results shown in FIG. 14 as a function of temperature in the range from 40° C. to 140° C.

EXAMPLE 8

Into a flask of 1 liter capacity with a separable cover equipped with a stirrer and thermometer were introduced 91.9 g of cyclopentanone, 243.20 g of o-cresol, 97.49 g of 35% concentrated hydrochloric acid and 8 ml of thioglycolic acid to form a reaction mixture which was agitated at 28° C. for 3 hours followed by standing as such for 24 hours to find that the reaction mixture was partly solidified into a slurry-like form. The reaction mixture was filtered with suction and the thus collected crystals were washed successively with 100 ml of water and 100 ml of m-xylene. After three times repetition of this washing procedure, the crystals were dried to give 169.04 g of white crystals as a product. The analytical results of this product by the $^1$H-NMR, $^{13}$C-NMR and GC-MS analyses indicated that this product was composed of a single compound which could be identified to be 1,1-bis(4-hydroxy-3-methyl phenyl) cyclopentane. The retention time of this compound in the gas chromatographic analysis (FID) was 7.7 minutes with a 50 meter long capillary column.

Figure 15A:
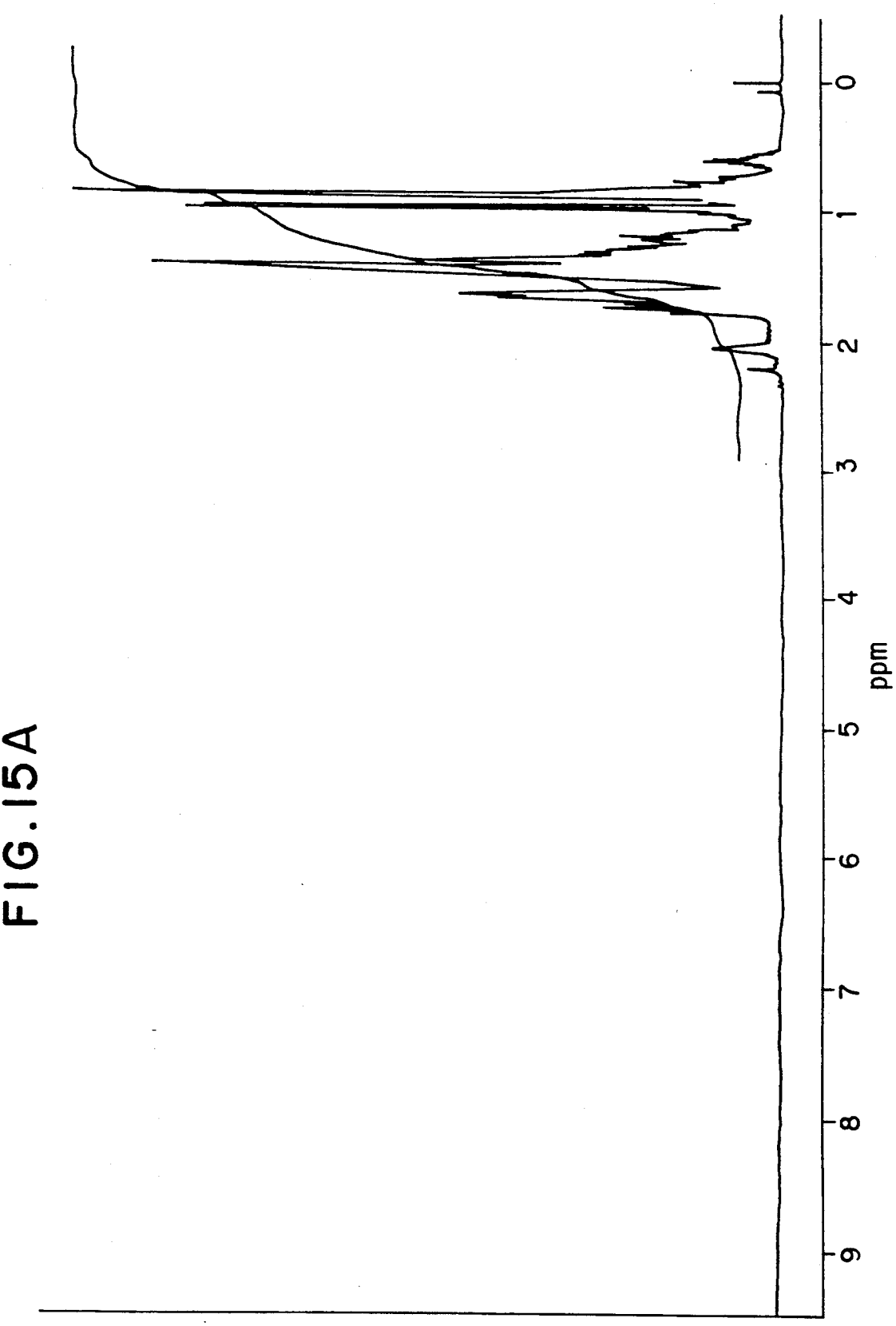
FIGS. 15A and 15B, 16 and 17 are a $^1$H-NMR diagram (solvent: CDCl$_3$), a $^{13}$C-NMR diagram (solvent: CDCl$_3$) and a GC-MS diagram, respectively of 1,1-di(3-methyl cyclohexyl) cyclopentane prepared in Example 8. The coordinates for FIGS. 17A and 17B are the same, but in FIG. 17B the peak heights are shown as ten times that of FIG. 17A.
Figure 15B:
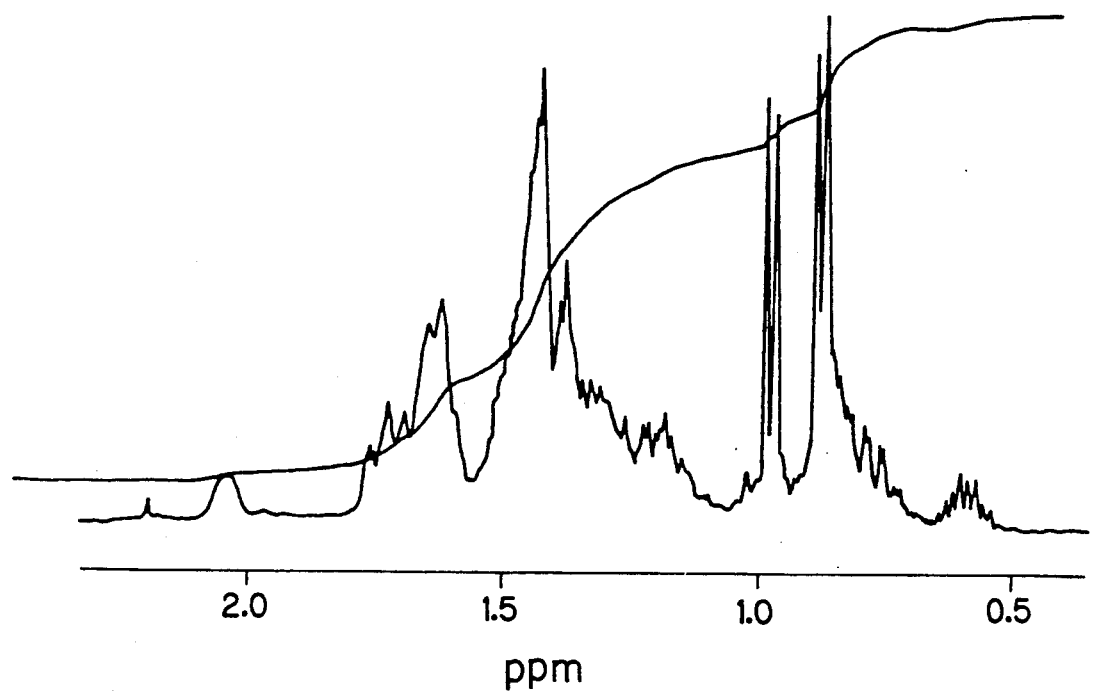
Figure 16:
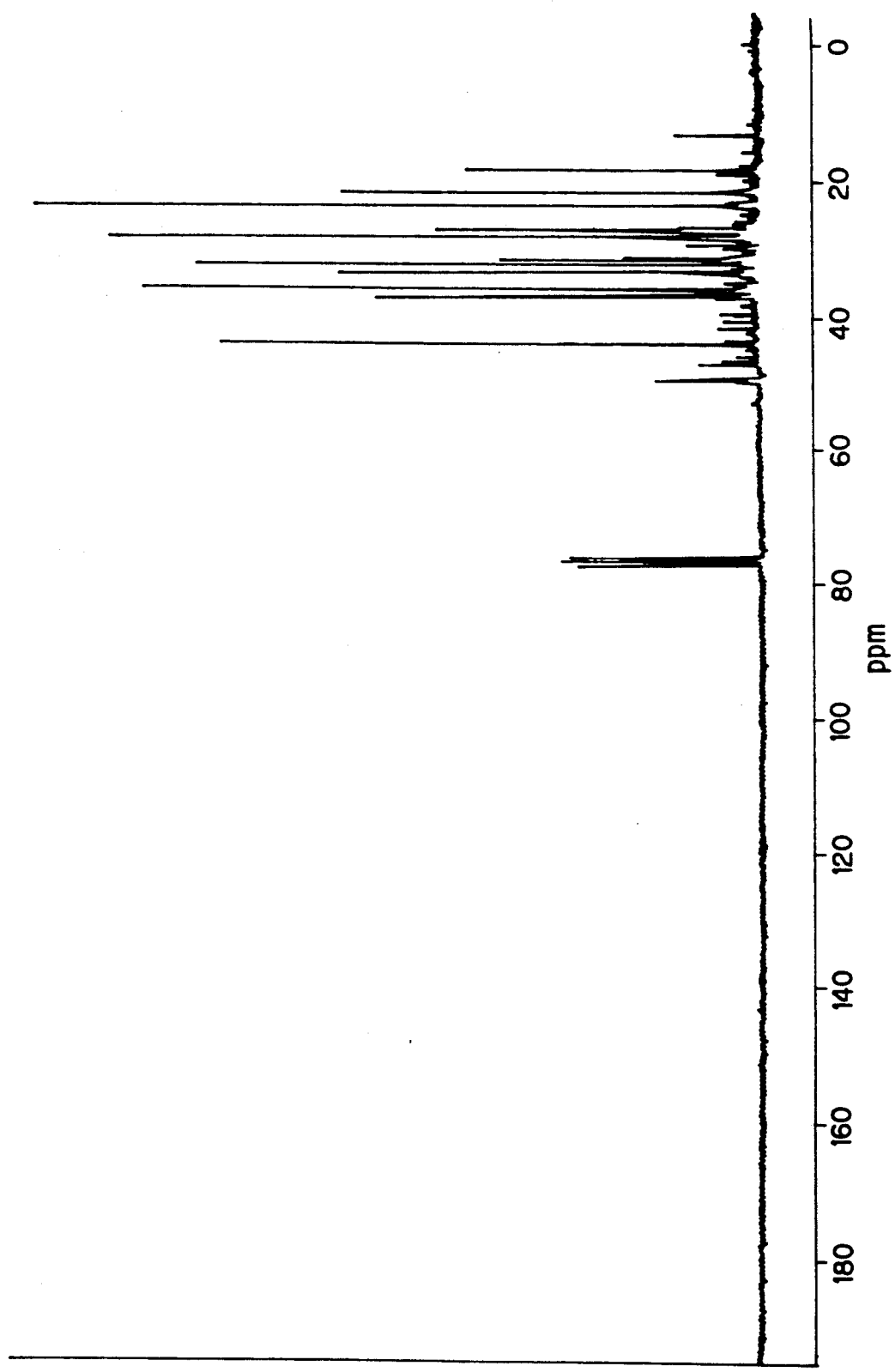
Figure 17B:
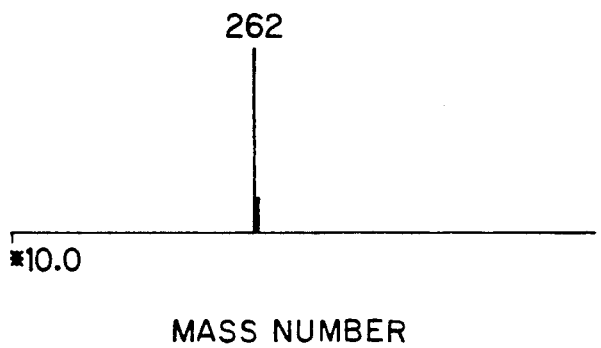

In the next place, 160 g of the thus obtained crystals were subjected to the reaction in the same manner as in Example 7. After completion of the reaction, the reaction mixture was processed in the same manner as in Example 7 to give 142.16 g of a product of which the analytical results indicated that the hydrogenation of the starting compound was at least 99.9% with complete disappearance of the hydroxy groups. This product could be identified to be 1,1-di(3-methyl cyclohexyl) cyclopentane $C_{19}H_{34}$ from the results of the $^1$H-NMR, $^{13}$C-NMR and GC-MS analyses. The retention time of this compound in the gas chromatographic analysis (FID) was 4.8 minutes. FIGS. 15, 16 and 17 show a $^1$H-NMR diagram, $^{13}$C-NMR diagram and GC-MS diagram, respectively, of this compound. This product had following physical properties.

Kinematic viscosity: 61.82 centistokes at 40° C.; 4.813 centistokes at 100° C.
Viscosity index: −241.
Specific gravity (15/4° C.): 0.9426.
Refractive index $n_D^{20}$: 1.5034.

Further, the traction coefficient of this product compound was determined to give the results shown in FIG. 14 as a function of temperature in the range from 40° C. to 140° C.

EXAMPLE 9

Into a flask of 1 liter capacity with a separable cover equipped with a gas blowing tube, stirrer and thermometer were introduced 112.06 g of norcamphor, 235.92 g of phenol and 12 ml of thioglycolic acid to form a reaction mixture which was heated at 70° C. for 6 hours under agitation while hydrogen chloride gas was blown thereinto so that the reaction mixture was converted into a dark brown solid. After interruption of blowing of hydrogen chloride gas, the reaction mixture was admixed with 200 ml of m-xylene and 250 ml of water and agitated at 70° C. for 1 hour so that the solid was disintegrated to precipitate crystals of light pink color. After cooling to room temperature, the reaction mixture was filtered with suction to collect the crystals which were washed successively with 100 ml of water and 100 ml of m-xylene. This washing procedure was repeated three times and the crystals were dried to give 163.55 g of white crystals. This product was found to be composed of a single compound and identified to be 2,2-bis(4-hydroxyphenyl) [2.2.1]-bicycloheptane from the results of the $^1$H-NMR, $^{13}$C-NMR and GC-MS analyses The retention time of this compound in the gas chromatographic analysis (FID) was 10.8 minutes with a 50 meter long capillary column.

Figure 18:
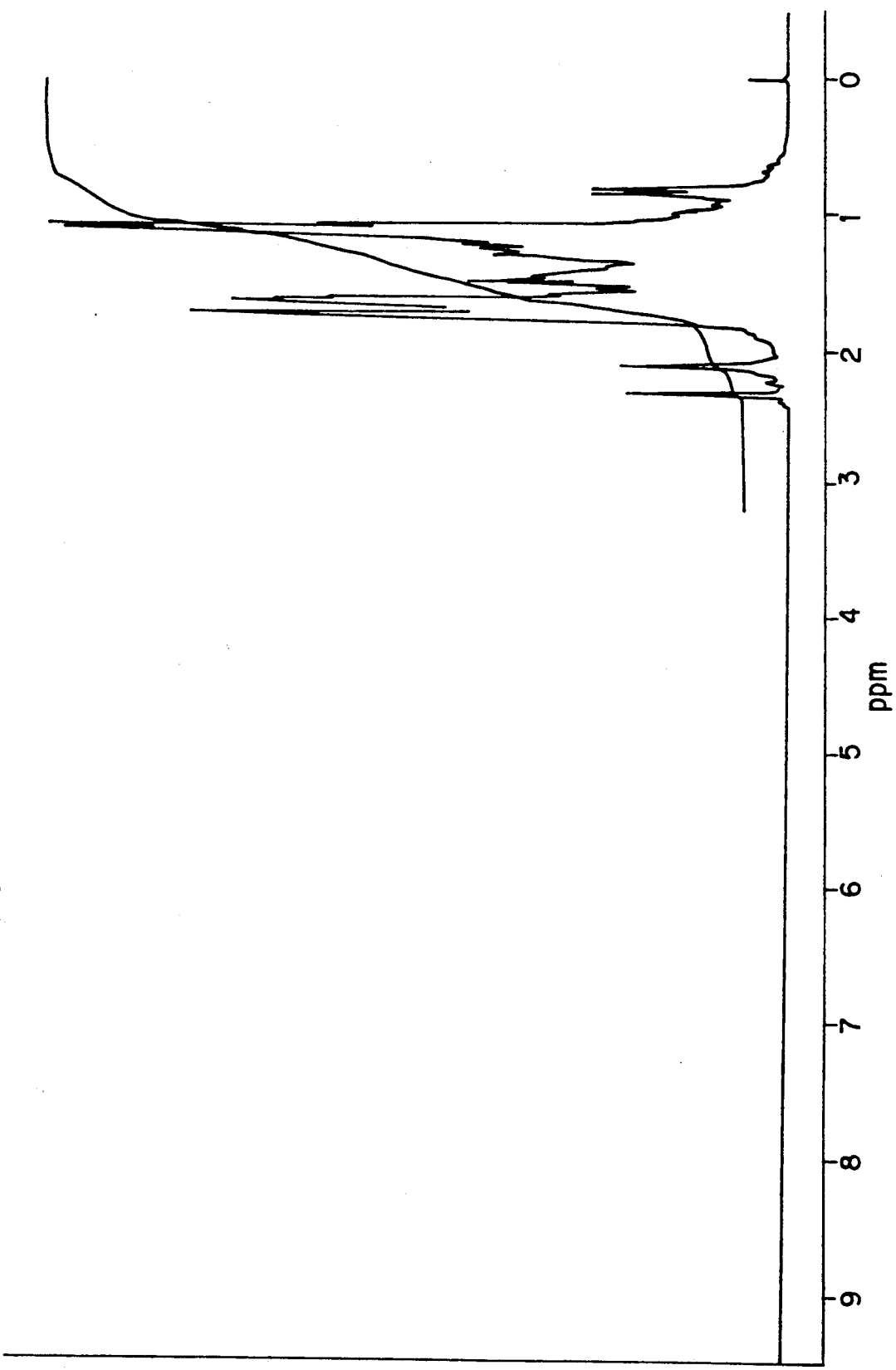
FIGS. 18, 19 and 20A and 20B are a $^1$H-NMR diagram (solvent: CDCl$_3$), a $^{13}$C-NMR diagram (solvent: CDCl$_3$) and a GC-MS diagram, respectively of 2,2-dicyclohexyl [2.2.1]-bicycloheptane prepared in Example 9. The coordinates for FIGS 20A and 20B are the same, but in FIG. 20B the peak heights are shown as ten times that of FIG. 20A.
Figure 19:
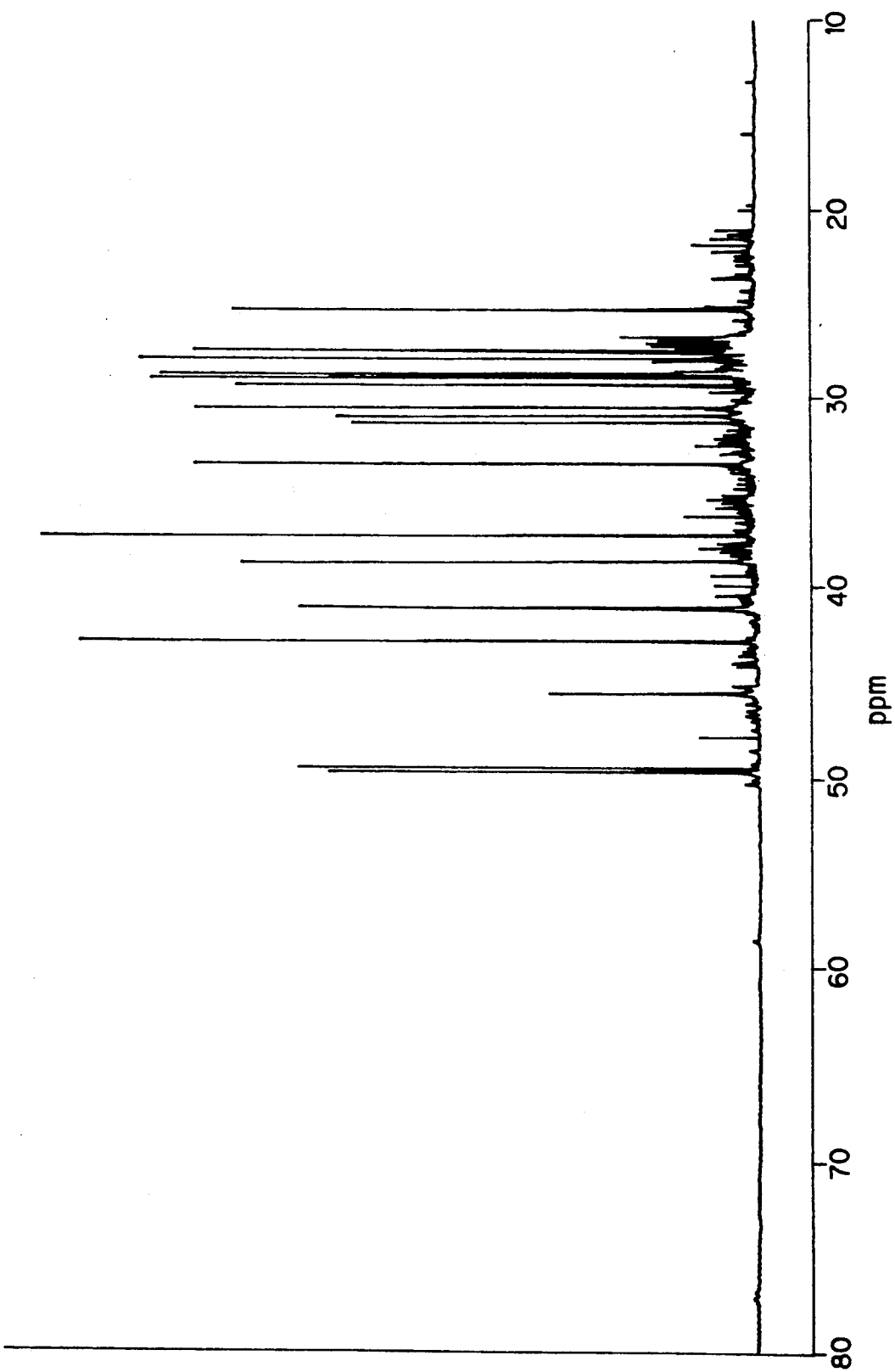
Figure 20A:
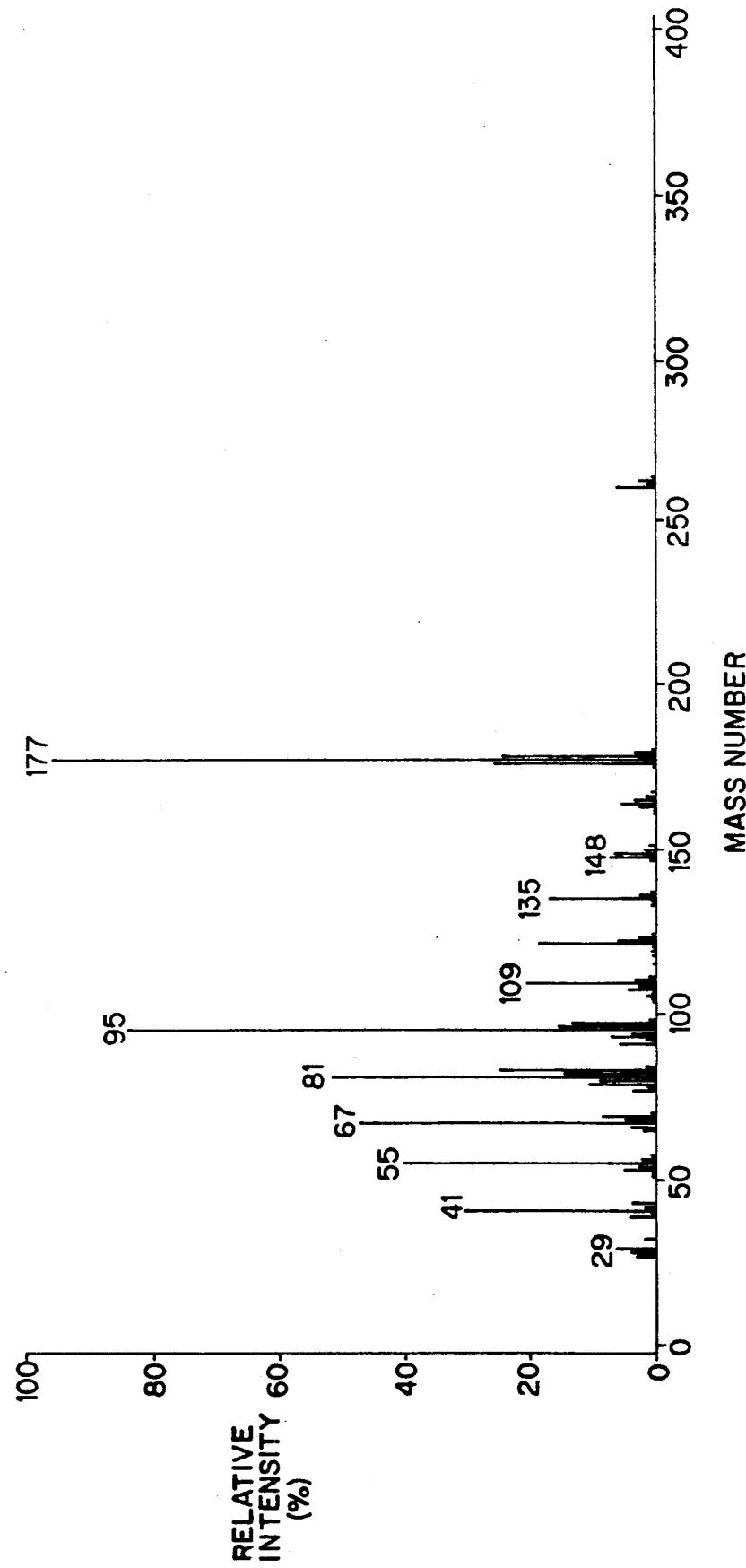
Figure 20B:
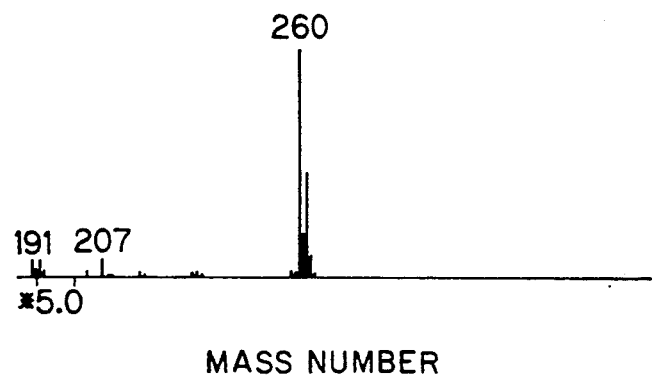

In the next place, 150 g of the thus obtained crystals were introduced into an autoclave of 1 liter capacity and subjected to the reaction in the same manner as in Example 7 except that the temperature in the final step was 220° C. instead of 215° C. After completion of the reaction, the reaction mixture was processed in the same manner as in Example 7 to give 135.21 g of a product of which the analytical results indicated that the hydrogenation of the starting compound was at least 99.9% with complete disappearance of the hydroxy groups, aromatic structure and olefinic unsaturation. This product compound could be identified to be 2,2-dicyclohexyl [2.2.1]-bicycloheptane from the results of the ¹H-NMR, ¹³C-NMR and GC-MS analyses. The retention time of this compound in the gas chromatographic analysis (FID) was 5.1 minutes. FIGS. 18, 19 and 20 show a ¹H-NMR diagram, ¹³C-NMR diagram and GC-MS diagram, respectively, of this compound. This product had following physical properties.

Kinematic viscosity: 99.90 centistokes at 40° C.; 6.772 centistokes at 100° C.

Viscosity index: −101.

Specific gravity (15/4° C.): 0.9819.

Refractive index $n_D^{20}$: 1.5200.

Further, the traction coefficient of this product was determined to give the results shown in FIG. 14 as a function of temperature in the range from 40° C. to 140° C.

EXAMPLE 10

Into a flask of 1 liter capacity with a separable cover equipped with a gas blowing tube, stirrer and thermometer were introduced 132.77 g of norcamphor, 325.33 g of o-cresol and 12 ml of thioglycolic acid to form a reaction mixture which was heated at 74° C. for 7 hours under agitation while hydrogen chloride gas was blown thereinto so that the reaction mixture was converted into a dark brown solid After interruption of blowing of hydrogen chloride gas, the reaction mixture was admixed with 200 ml of m-xylene and 200 ml of water and agitated at 70° C. for 1 hour so that the solid was disintegrated to give a slurried suspension of light pink color After cooling to room temperature, the suspension was filtered with suction to collect the crystals which were washed successively with 100 ml of water and 100 ml of m-xylene. After three times repetition of this procedure of washing, the crystals were dried to give 156.80 g of white crystals This product was found to be composed of a single compound and could be identified to be 2,2-bis(4-hydroxy-3-methyl phenyl) [2.2.1]-bicycloheptane from the results of the ¹H-NMR, ¹³C-NMR and GC-MS analyses. The retention time of this compound in the gas chromatographic analysis (FID) was 11.7 minutes with a 50 meter long capillary column.

Figure 21A:
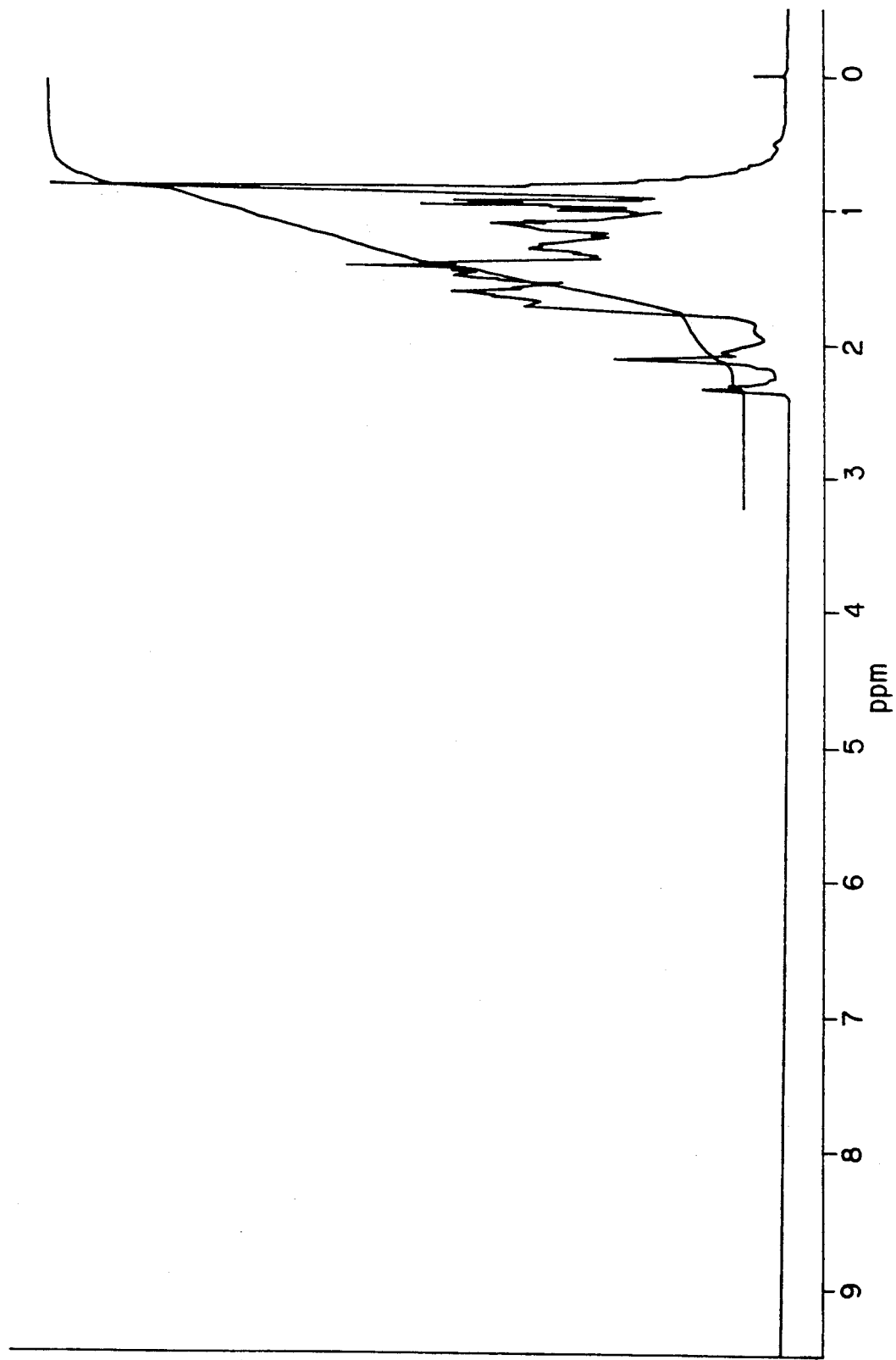
FIGS. 21A and 21B, 22 and 23A and 23B are a $^1$H-NMR diagram (solvent: CDCl$_3$), a $^{13}$C-NMR diagram (solvent: CDCl$_3$) and a GC-MS diagram, respectively of 2,2-di(3-methyl cyclohexyl) [2.2.1]-bicycloheptane prepared in Example 10. The coordinates for FIGS. 23A and 23B are the same, but in FIG. 23B the peak heights are shown as ten times that of FIG. 23A.
Figure 21B:
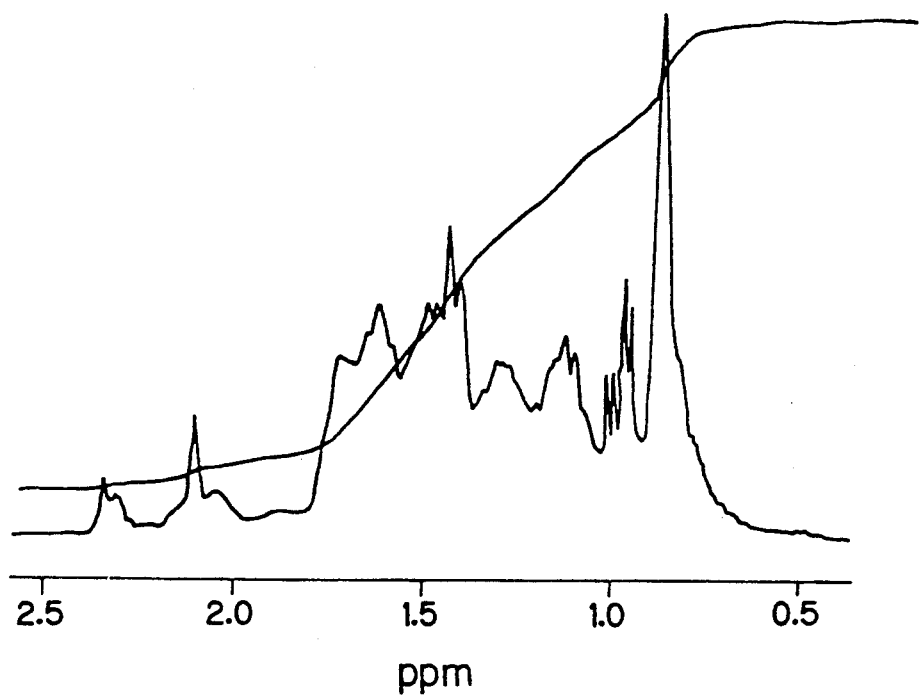
Figure 22:
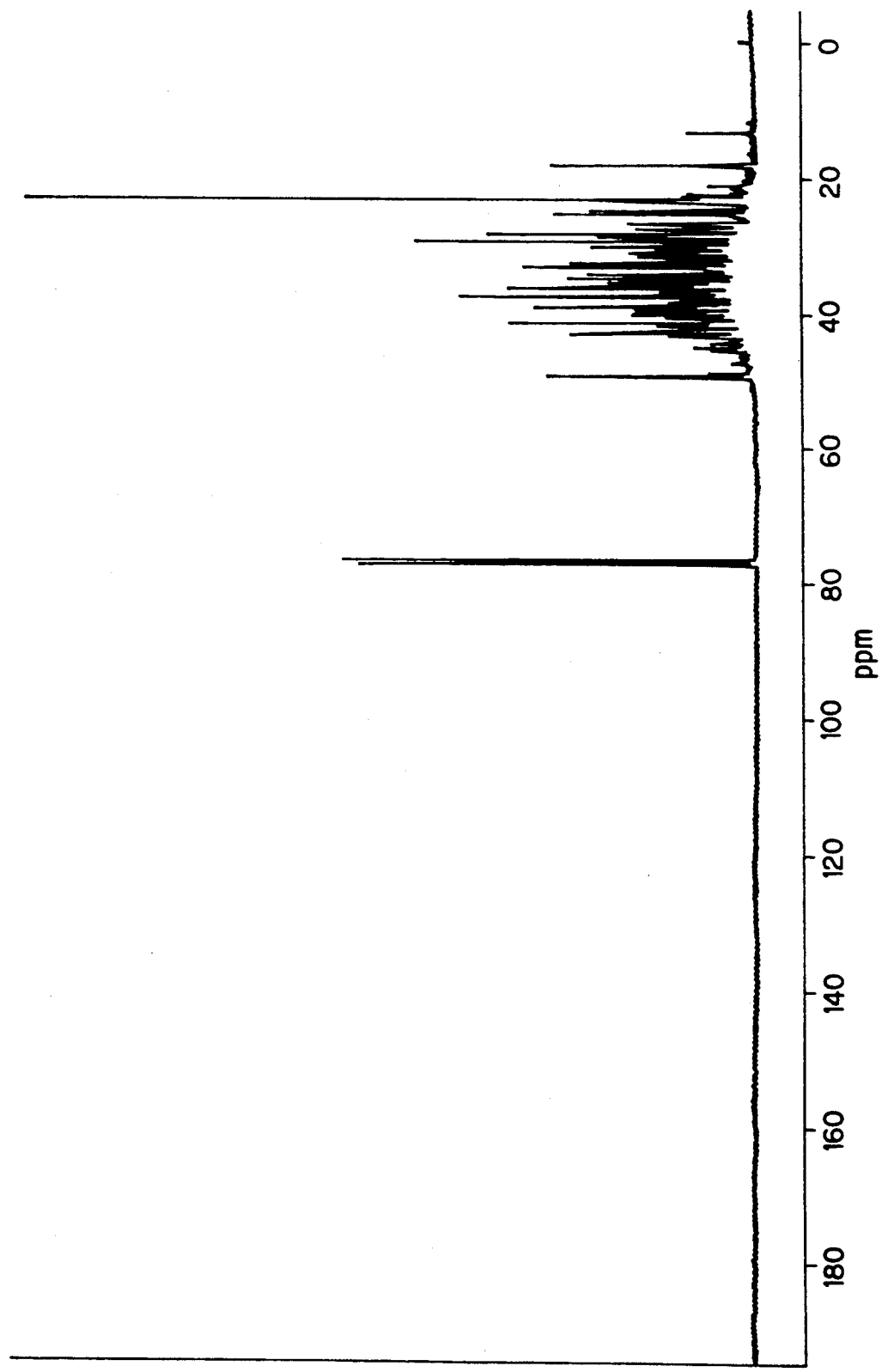
Figure 23A:
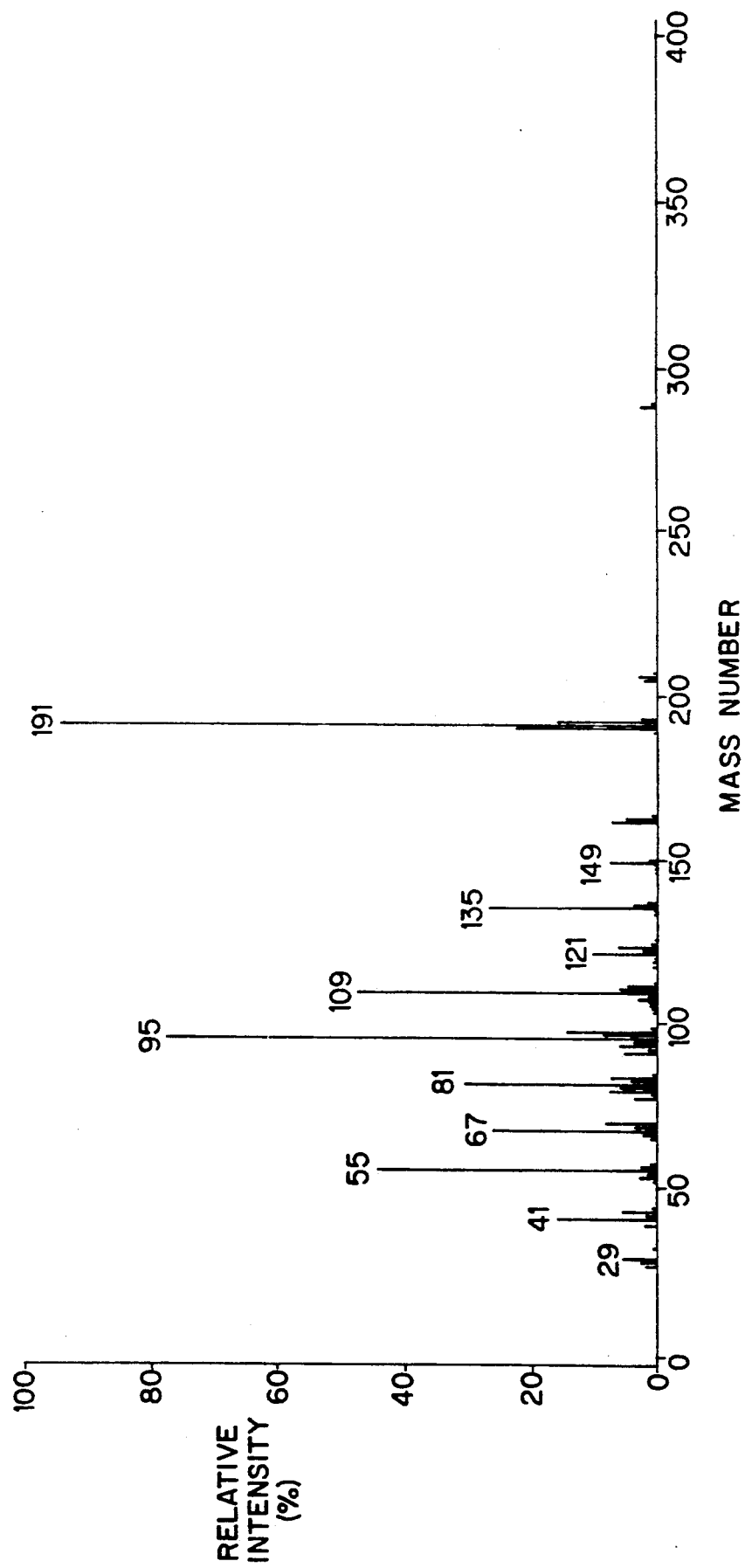
Figure 23B:
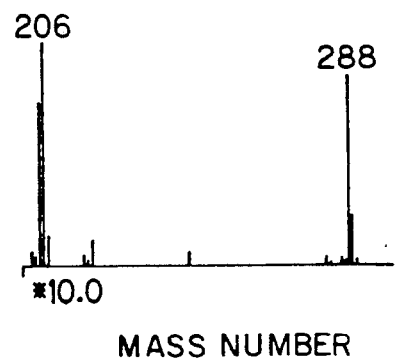

In the next place, 150 g of the thus obtained crystals were subjected to the reaction in the same manner as in Example 9 and, after completion of the reaction, the reaction mixture was processed in the same manner as in Example 7 to give 131.56 g of a product which was identified to be composed of a single compound with complete disappearance of hydroxy groups, aromatic structure and olefinic unsaturation from the results of analysis This compound was identified to be 2,2-di(3-methyl cyclohexyl)[2.2.1]-bicycloheptane $C_{21}H_{36}$ from the results of the ¹H-NMR, ¹³C-NMR and GC-MS analyses. The retention time of this compound in the gas chromatographic analysis (FID) was 5.4 minutes. FIGS. 21, 22 and 23 show a ¹H-NMR diagram, ¹³C-NMR diagram and GC-MS diagram, respectively, of this compound. This product had following physical properties.

Kinematic viscosity: 230.2 centistokes at 40° C.; 8.337 centistokes at 100° C.

Viscosity index: −277.

Specific gravity (15/4° C.): 0.9660.

Refractive index $n_D^{20}$: 1.5135.

Further, the traction coefficient of this product was determined to give the results shown in FIG. 14 as a function of temperature in the range from 40° C. to 140° C.

As is described above, the present invention provides an efficient method for the preparation of various kinds of 1,1-dicyclohexyl cycloalkane derivatives as a class of novel compounds. These compounds generally have a low viscosity and high traction coefficient over a wide temperature range from room temperature to elevated temperatures. These unique properties of the inventive compound as a traction-drive fluid give a possibility of constructing a traction drive apparatus of a compact and light-weight design with an increase in the serviceable life of the apparatus even when the apparatus is driven under adverse conditions.

What is claimed is:

1. A 1,1-dicyclohexyl cycloalkane derivative represented by the general formula

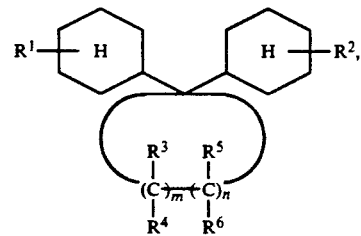

in which $R^1$ and $R^2$ are each, independently from the other, a hydrogen atom or a lower alkyl group, $R^3$, $R^4$, $R^5$ and $R^6$ are each, independently from the others, a hydrogen atom, a lower alkyl group or an alkylene group forming a ring structure together with either one of the others and the carbon atom in the cycloalkane ring to which the group is bonded, and the subscripts m and n are each zero or a positive integer not exceeding 6 with the proviso that m+n is 4, 5 or 6.

2. A method for the preparation of a 1,1-dicyclohexyl cycloalkane derivative represented by the general formula

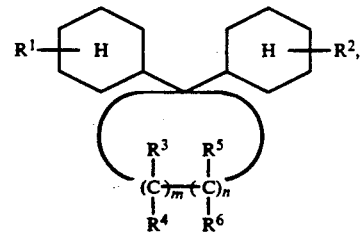

in which $R^1$ and $R^2$ are each, independently from the other, a hydrogen atom or a lower alkyl group, $R^3$, $R^4$, $R^5$ and $R^6$ are each, independently from the others, a hydrogen atom, a lower alkyl group or an alkylene group forming a ring structure together with either one of the others and the carbon atom in the cycloalkane ring to which the group is bonded, and the subscripts m and n are each zero or a positive integer not exceeding 6 with the proviso that m+n is 4, 5 or 6, which comprises the step of:

subjecting a 1,1-di(hydroxyphenyl) cycloalkane compound represented by the general formula

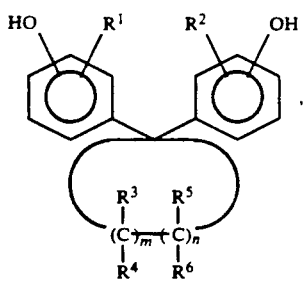

in which each of the symbols has the same meaning as defined above, to a hydrogenation reaction and a dehydration reaction in combination in the simultaneous presence of a hydrogenation catalyst and a dehydration catalyst.

3. A method for the preparation of a 1,1-dicyclohexyl cycloalkane derivative represented by the general formula

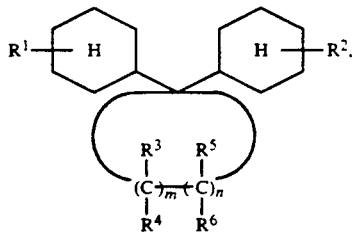

in which $R^1$ and $R^2$ are each, independently from the other, a hydrogen atom or a lower alkyl group, $R^3$, $R^4$, $R^5$ and $R^6$ are each, independently from the others, a hydrogen atom, a lower alkyl group or an alkylene group forming a ring structure together with either one of the others and the carbon atom in the cycloalkane ring to which the group is bonded, and the subscripts m and n are each zero or a positive integer not exceeding 6 with the proviso that m+n is 4, 5 or 6, which comprises the steps of:

(a) subjecting a 1,1-di(hydroxyphenyl) cycloalkane compound represented by the general formula

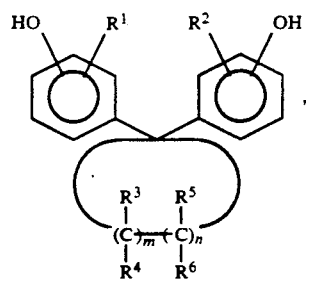

in which each of the symbols has the same meaning as defined above, to a hydrogenation reaction to give a 1,1-di(hydroxy cyclohexyl) cycloalkane compound represented by the general formula

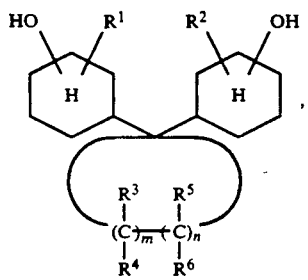

in which each of the symbols has the same meaning as defined above; and (b) subjecting the 1,1-di(hydroxy cyclohexyl) cycloalkane compound obtained in step (a) to a dehydration reaction and a hydrogenation reaction in combination.

4. A traction-drive fluid which comprises at least 1% by weight of a 1,1-dicyclohexyl cycloalkane derivative represented by the general formula

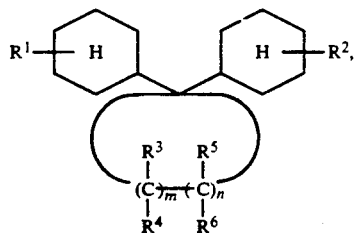

in which $R^1$ and $R^2$ are each, independently from the other, a hydrogen atom or a lower alkyl group, $R^3$, $R^4$, $R^5$ and $R^6$ are each, independently from the others, a hydrogen atom, a lower alkyl group or an alkylene group forming a ring structure together with either one of the others and the carbon atom in the cycloalkane ring to which the group is bonded, and the subscripts m and n are each zero or a positive integer not exceeding 6 with the proviso that m+n is 4, 5 or 6.

5. The method for the preparation of a 1,1-dicyclohexyl cycloalkane derivative as claimed in claim 2 wherein the reaction is performed at a temperature in the range from room temperature to 220° C. under a hydrogen pressure in the range from 5 kg/cm$^2$G to 150 kg/cm$^2$G.

6. The traction-drive fluid as claimed in claim 4 which comprises from 5% by weight to 60% by weight of the 1,1-dicyclohexyl cycloalkane derivative.

* * * * *